(12) United States Patent
Garner et al.

(10) Patent No.: US 9,078,621 B2
(45) Date of Patent: Jul. 14, 2015

(54) METHOD AND SYSTEM OF MEASURING ANATOMICAL FEATURES IN SUBCUTANEOUS IMAGES TO ASSESS RISK OF INJURY

(71) Applicants: BAYLOR UNIVERSITY, Waco, TX (US); SCOTT & WHITE HEALTHCARE, Temple, TX (US)

(72) Inventors: Brian A. Garner, Waco, TX (US); Christopher Chaput, Temple, TX (US); Jacob Hoffman, Waco, TX (US)

(73) Assignees: Baylor University, Waco, TX (US); Scott & White Healthcare, Temple, TX (US)

( * ) Notice: Subject to any disclaimer, the term of this patent is extended or adjusted under 35 U.S.C. 154(b) by 48 days.

(21) Appl. No.: 14/074,980

(22) Filed: Nov. 8, 2013

(65) Prior Publication Data
US 2014/0133726 A1    May 15, 2014

Related U.S. Application Data

(60) Provisional application No. 61/724,711, filed on Nov. 9, 2012.

(51) Int. Cl.
*G06T 7/00* (2006.01)
*A61B 5/00* (2006.01)
*G06T 7/60* (2006.01)

(52) U.S. Cl.
CPC .............. *A61B 5/4504* (2013.01); *G06T 7/0012* (2013.01); *G06T 7/0014* (2013.01); *G06T 7/60* (2013.01); *G06T 2207/10081* (2013.01); *G06T 2207/30012* (2013.01)

(58) Field of Classification Search
USPC .......................................................... 382/131
See application file for complete search history.

(56) References Cited

PUBLICATIONS z0mbie.host, Injuries of the Cervicocranium, 2009, p. 7-8, Retrived from the Internet on Feb. 26, 2015; retrieved from URL: <http://z0mbie.host.sk/Injuries-of-the-Cervicocranium.html>.*
Chaput, Christopher D. et al., "Defining and detecting missed ligamentous injuries of the occipitocervical complex." Spine 36, No. 9 (2011): 709-714.*
PCT International Search Report from PCT Application No. PCT/US13/69171 dated Feb. 17, 2014.
S Rueda et al., "An approach for the automatic cephalometric landmark detection using mathematical morphology and active appearance models", Jan. 1, 2006, Medical Image Computing and Computer-Assisted Intervention—MICCAI 2006, 159-166.

* cited by examiner

*Primary Examiner* — Gregory F Cunningham
(74) *Attorney, Agent, or Firm* — Locke Lord LLP

(57) ABSTRACT

The present disclosure provides a method and system using software and associated equipment to automatically identify two or more preselected anatomical features by examining pixels within images such as computerized tomography (CT) scanned images, determining appropriate measurements between such identified features based on dimensions and scaling available within the image file, comparing these measurements to normative data, and providing output of the results to a user, such as medical personnel. In at least one embodiment, system can measure the basion-dens interval (BDI), which has been shown to be an effective indicator of ligament injury within the occipito-cervical complex ("OCC") that may not present with other symptoms, is not revealed with standard CT imaging, and is of mortal danger to the patient if untreated. The system can automate interpreting CT scanned images and alert medical personnel about the risk of OCC ligament damage.

25 Claims, 19 Drawing Sheets

Star

C2

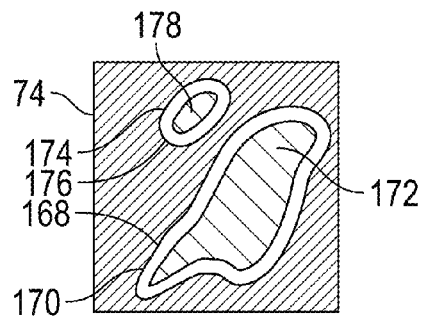
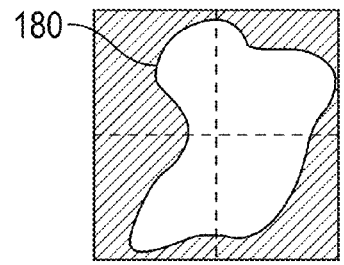
FIG. 30A  FIG. 30B
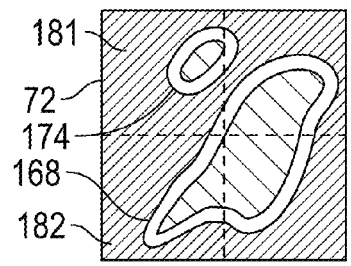
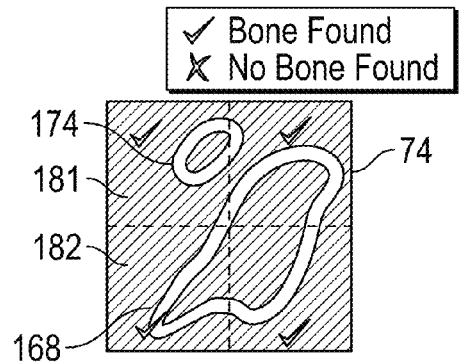
FIG. 30C  FIG. 30D
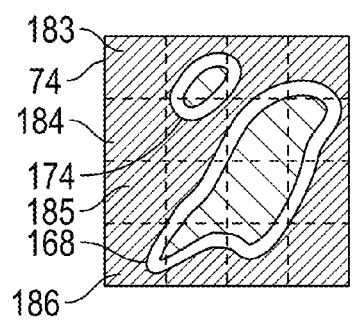
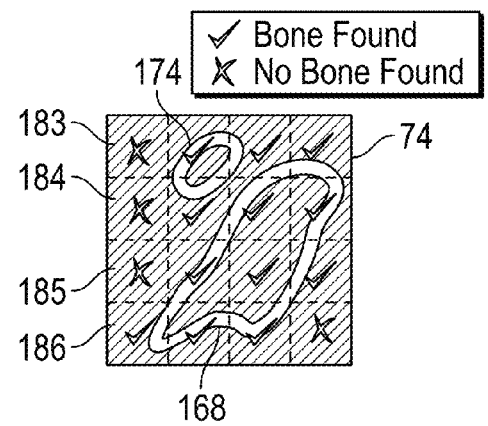
FIG. 30E  FIG. 30F

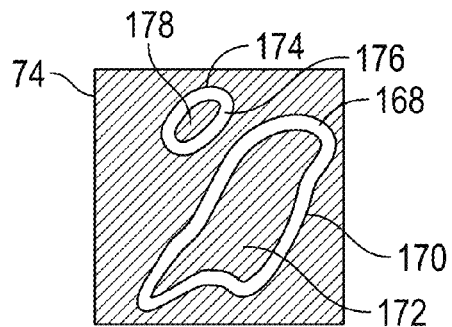 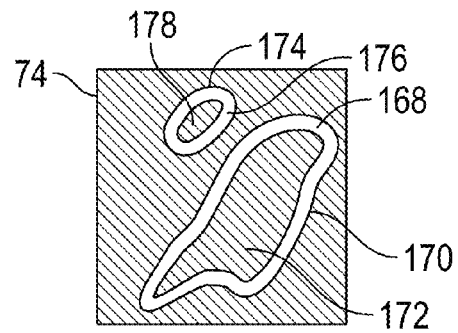
FIG. 31A    FIG. 31B
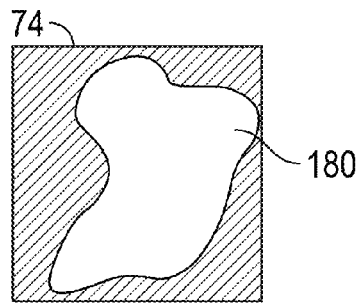 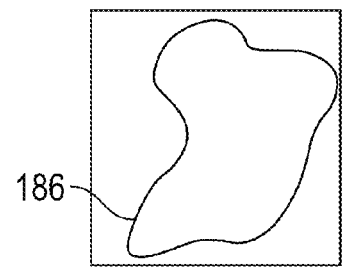
FIG. 32A    FIG. 32B
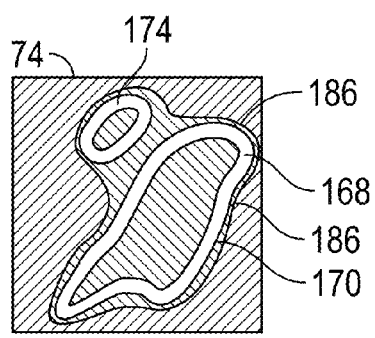 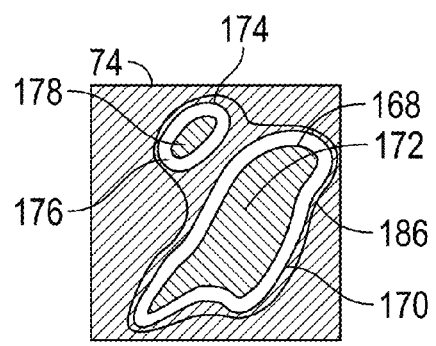
FIG. 33A    FIG. 33B

METHOD AND SYSTEM OF MEASURING ANATOMICAL FEATURES IN SUBCUTANEOUS IMAGES TO ASSESS RISK OF INJURY

CROSS REFERENCE TO RELATED APPLICATIONS

This application claims the benefit of U.S. Provisional Appl. No. 61/724,711 filed on Nov. 9, 2012 and is incorporated herein by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The invention disclosed and taught herein relates generally to a method and system of locating and/or tracing along pre-selected anatomical features that includes processing digital images of the general region of the structures to locate the specific features, mathematically determining a distance between such features, comparing the determined distance to normative data, and reporting the results. More specifically, the invention can be used to determine a distance between anatomical features from analyzed subcutaneous images such as computerized tomography (CT) scans, comparing the distance to normative data for possible ligament damage, and reporting the results.

2. Description of the Related Art

FIG. 1 is a prior art drawing of an exemplary skull of a human showing anatomical regions. FIG. 2 is a prior art drawing of an inferior view of the bottom of the skull showing the basion and foramen magnum. FIG. 3 is a prior art perspective drawing of a first vertebra ("atlas") located above the second vertebra ("axis") with a dens and a vertebral foramen. FIG. 4 is a prior art exemplary CT scanned image in a sagittal plane of a typical skull showing anterior and posterior portions of the skull and the basion on the skull located above the dens on the axis. The figures will be described in conjunction with each other. The reference orientations and directions shown in the figures are based on customary medical orientations for imaging and include the following positions relative to a chosen datum, for example, the skull as shown in FIG. 1: a superior position 6 is upwardly disposed, an inferior position 8 is downwardly disposed, an anterior position 10 is forwardly disposed, and a posterior position 12 is rearwardly disposed. For purposes herein, the following axes are defined. The X-axis is oriented horizontally in the images (toward the right image side) and corresponds to the posterior anatomical direction. The Y-axis is oriented vertically in the images (toward the top of the image) and corresponds to the superior anatomical direction. These axis definitions are consistent with common use in current medical practice. Expanding these definitions to three dimensions, the Z-axis is oriented perpendicular to the sagittal (X-Y) plane of the images (and pointing outward from the image plane), and corresponds to a lateral, leftward anatomical direction. A Z-X plane is shown in FIG. 5.

The skull 2 has a region known as the occipital region 4 that extends from the back of the skull to an underneath position adjacent the mandible. An occipito-cervical complex (OCC) is defined as the region extending from below occipital region 4 (FIGS. 1 and 2) to the second cervical interspace 29 (FIG. 3) that is between first and second vertebra of the neck and thus includes the region of the vertebra that connects to the skull. A first vertebra 18 is rigidly connected with the skull 2 with the portion 22 pointed outwardly from the page of FIG. 3 in a posterior direction. A second vertebra 24 is rotatably coupled with the first vertebra 18 with the cervical interspace 29 therebetween, with the portion 28 pointed outwardly from the page of the figure in a posterior direction. An opening known as a foramen magnum 14 in the skull 2 at the occipital region 4 is aligned with a corresponding opening in the vertebra known as a vertebral foramen 20 and the opening through which the spinal cord enters the back of the skull. The first vertebra 18 is also known as the "atlas" and the second vertebra 24 is also known as the "axis" in reference to their relative functions.

An inferior portion of the skull 2 is the basilar part with the basion 16 adjacent the spine and associated vertebra 18, 24. The inferior-protruding basion 16 is the mid-point on the anterior margin of the foramen magnum 14 at the base of the skull 2 where the skull articulates with the first cervical vertebra (atlas) 18. The dens 26 is a protuberance on the anterior portion of the second cervical vertebra (axis) 24. The dens 26 protrudes in a superior direction through the first cervical vertebra 18 that is connected with the skull 2, and is connected through ligaments with the basion 16 of the occipital region 4.

High-energy deceleration force often associated with motor vehicle collisions can compromise the stability provided by the strong OCC ligaments and result in spinal cord injury and death. With recent, improved pre-hospital care, the number of patients surviving such injuries and needing definitive management has increased. Some of these patients present neurologically intact, but if the OCC damage is not quickly and properly diagnosed and treated it can progress quickly and catastrophically.

FIG. 5 is a prior art bottom view (anatomical axial view) schematic showing the skull foramen magnum with an edgewise view of sagittal plane images and their positions along the medio-lateral dimension, which images can be used to locate internal anatomical regions and features. Computerized tomography (CT) scans are commonly performed on the head of a patient transversely across the body line longitudinal axis at different depths in the X-Z plane. Then, commercially-available imaging software can reconstruct images in other planes from the original set. One type of resulting images is known as the "sagittal plane" images that are created in an orientation longitudinally along the body axis, that is, aligned in the X-Y plane of FIG. 4 and appearing as lines in FIG. 5. Thus, FIG. 5 shows the edges of sagittal-plane adjacent exemplary images 30-46 at different depths along a Z-axis. The images are used routinely in polytrauma patients and are effective at revealing cervical fractures, but may not reveal damage to soft tissues such as ligaments. Injury to the OCC ligaments can be difficult to detect. Research from those in the field, such as Dr. Christopher D. Chaput, MD in "Defining and Detecting Missed Ligamentous Injuries of the Occipitocervical Complex," Spine, Vol. 36, No. 9, pp. 709-714 (2011), has determined that measurements of the OCC skeletal anatomy, including distances and alignments between certain skeletal landmarks, when compared with high quality normative data, can be used to detect ligamentous injury in the OCC that may otherwise be missed. However, accurately identifying the skeletal landmarks and properly interpreting the scans requires unusual care, training, and expertise.

According to the research of comparing measurements of the OCC skeletal anatomy with high quality normative data, the measurement of primary importance is the basion-dens interval (BDI), which is the linear distance from the inferior-most position of the basion to the superior-most position of the dens. If this distance exceeds a certain threshold, then the potential risk of undetected OCC injury is substantially elevated. Currently, the BDI is determined through visual inspection, usually by a physician and/or radiologist viewing a patient's CT scans or other radiologic images. The physician or radiologist manually identifies the image or images that best show the extrema points of the basion and the dens, and then uses those images to measure the BDI. Such a manual determination, however, is tedious, time-consuming, and susceptible to human error, despite the highest level of medical training, skill, and experience.

Therefore, there remains a need to provide a method and system of automatically detecting the distance between the dens and basion, and indicating automatically whether there is an elevated risk of injury.

BRIEF SUMMARY OF THE INVENTION

The invention disclosed and taught herein relates generally to a method and system for automatically analyzing medical images, such as computerized tomography (CT) scans, for the purpose of detecting abnormal anatomical geometry that may indicate the presence of injury, such as ligament damage. The method and system identifies and measures anatomical features or landmarks of interest in a process that generally involves locating one or more anatomical bodies, such as bones, either by automatic means or by user selection, tracing along the perimeter of each anatomical body to find specific anatomical features of interest, computing geometric measures based on these features, comparing the computed measures with normative data, and reporting the results. As an exemplary case, the herein description will focus on automatic measurement of the basion-dens interval (BDI), which length may indicate life-threating injuries to the cervical spine ligaments following trauma such as during a motor vehicle accident.

The present disclosure provides a method and system using software and associated equipment to automatically identify two or more preselected anatomical features by examining pixels within images such as computerized tomography (CT) scanned images, determining appropriate measurements between such identified features based on dimensions and scaling available within the image file, comparing these measurements to normative data, and providing output of the results to a user, such as medical personnel. In at least one embodiment, the system can compute the basion-dens interval (BDI), which has been shown to be an effective indicator of ligament injury within the occipito-cervical complex ("OCC") that may not present with other symptoms, is not revealed with standard CT imaging, and is of mortal danger to the patient if untreated. The system can automate interpreting CT scanned images and alert medical personnel about the risk of OCC ligament damage.

The disclosure provides a method of determining a basion-dens interval from a set of digital images of an occipital-cervical area, comprising: identifying a first anatomical region in proximity to a basion; identifying a first bone in the first anatomical region coupled to the basion; processing a first image of the set of digital images comprising electronically searching along the first bone by progressively searching for bone pixels to determine a first image position of a preselected portion of the basion; identifying a second anatomical region in proximity to a dens; identifying a second bone in the second anatomical region coupled to the dens; processing the first image of the set of digital images comprising electronically searching along the second bone by progressively searching for bone pixels to determine a first image position of the preselected portion of the dens; repeating the processing of the first image on a second image of the set of digital images to find a second image position of the preselected portion of the basion and a second image position of the preselected portion of the dens, the first and second images defining a processed first subset of images; compiling the first and second image positions of the preselected portions of basion and the first and second image positions of the preselected portions of the dens to produce a compiled position of the preselected portion of the basion and a compiled position of the preselected portion of the dens from the subset of images, wherein the compiling comprises comparing the first and second image positions of the preselected portion of the basion and first and second image positions of the preselected portion of the dens in the subset of images; and computing a distance between the preselected portions of the basion and the preselected portion of the dens from the compiled position of the preselected portion of the basion and the compiled position of the preselected portion of the dens to establish a computed basion-dens interval ("BDI").

The disclosure provides a method of determining a basion-dens interval from a set of digital images of an occipital-cervical area, comprising: processing a first image of the set of images, which comprises: identifying a first anatomical region in proximity to a basion; electronically searching in a first direction to find a bone pixel that defines a first bone; electronically searching along the first bone in a second direction by progressively searching for bone pixels to determine a first image position of a preselected portion being an inferior portion of the basion; identifying a second anatomical region in proximity to a dens; electronically searching in a third direction to find a bone pixel that defines a second bone in the second anatomical region; and electronically searching along the second bone in a fourth direction by progressively searching for bone pixels to determine a first image position of a preselected portion being a superior portion of the dens. The method further comprises: changing to at least a second image of the set of images and repeating the processing steps for the second image to find a second image position of the preselected portion of the basion and a second image position of the preselected portion of the dens so that with at least the first image, the processing forms a processed subset of images; and compiling results from the processed subset of images to find a compiled position of the preselected portion of the basion and a compiled position of the preselected portion of the dens from the subset of images, which comprises: comparing image positions of at least two of the images in the subset of images; and selecting the position of the preselected portion of the basion and the position of the preselected portion of the dens from the image positions that minimizes a distance between the basion and the dens. The method further comprises computing a distance between the preselected portion of the basion and the preselected portion of the dens to establish a computed basion-dens interval ("BDI").

BRIEF DESCRIPTION OF THE SEVERAL
VIEWS OF THE DRAWINGS

FIG. 30A is a schematic partial image of an exemplary anatomical region.

FIG. 30B is a schematic exemplary first digital image of the image of FIG. 30A after a first processing pass using a predetermined intensity threshold.

FIG. 30C is a schematic subdivided digital image of the image of FIG. 30A.

FIG. 30D is a schematic exemplary second digital image of the image of FIG. 30C after a second processing pass with the intensity threshold determined per selected subdivision.

FIG. 30E is a schematic further subdivided digital image of the image of FIG. 30D.

FIG. 30F is a schematic exemplary a further digitally processed image of the image of FIG. 30E after a third processing pass with the intensity threshold determined per selected subdivision.

FIG. 31A is a schematic digital image showing the results of the processing of the image of FIG. 30F.

FIG. 31B is a schematic digital image of the image of FIG. 31A with a change in attributes.

FIG. 32A is the schematic image of FIG. 30B without the subdivisions.

FIG. 32B is a schematic image of edge pixels of the anatomical region shown in FIG. 32A.

FIG. 33A is a schematic image of the edge pixels of FIG. 32B mapped with the anatomical reference shown in FIG. 31.

FIG. 33B is a schematic image of FIG. 33A replacing pixels of an attribute with another attribute.

DETAILED DESCRIPTION

Figure 1:
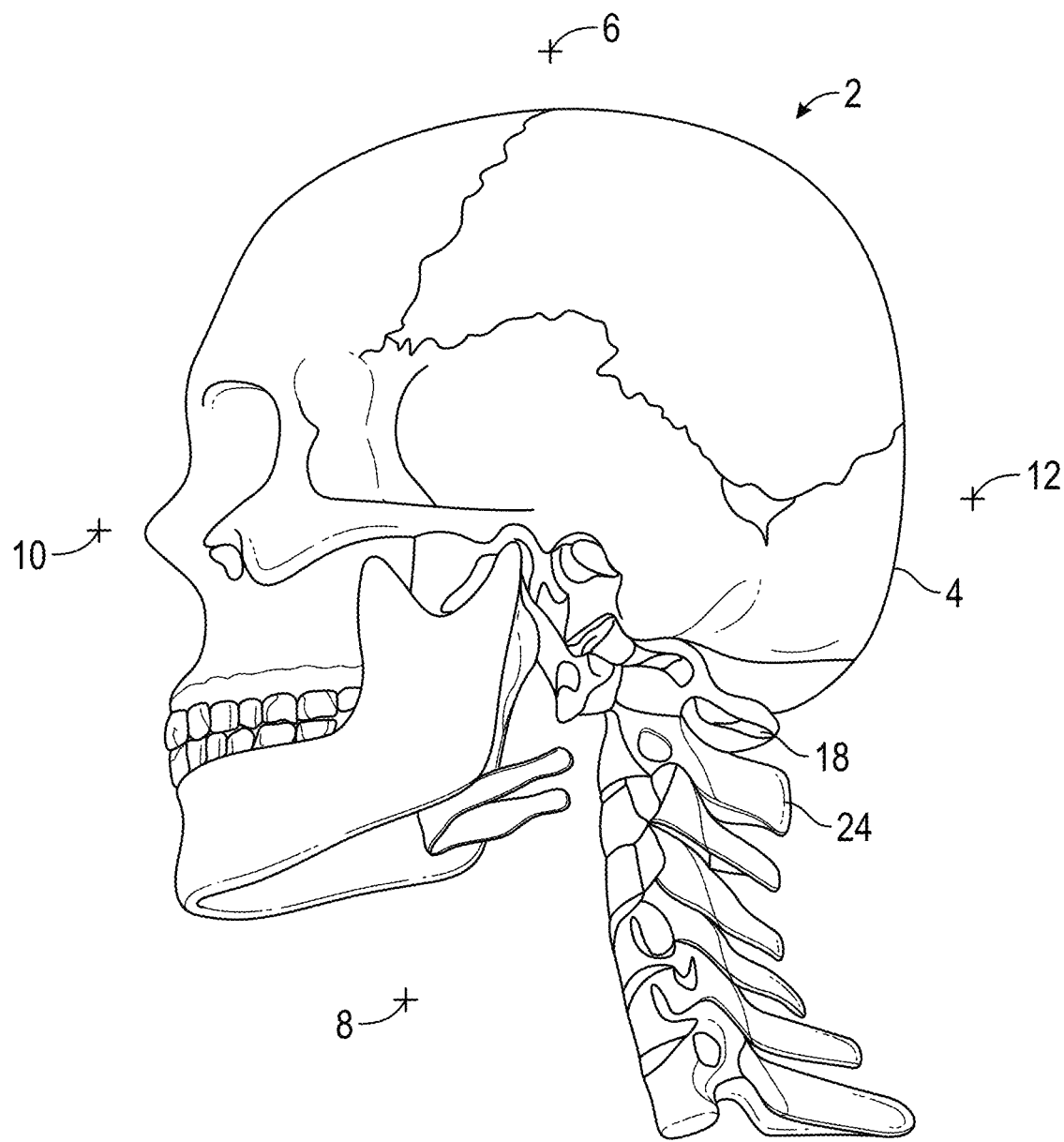
FIG. 1 is a prior art drawing of an exemplary skull of a human showing anatomical regions.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, position and from time to time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims. Where appropriate, elements have been labeled with an "a" or "b" to designate one side of the system or another. When referring generally to such elements, the number without the letter is used. Further, such designations do not limit the number of elements that can be used for that function.

The present disclosure provides a method and system using software and associated equipment to automatically identify two or more preselected anatomical features by examining pixels within images such as computerized tomography (CT) scanned images, determining appropriate measurements between such identified features based on dimensions and scaling available within the image file, comparing these measurements to normative data, and providing output of the results to a user, such as medical personnel. In at least one embodiment, the system can measure the basion-dens interval (BDI), which has been shown to be an effective indicator of ligament injury within the occipito-cervical complex ("OCC") that may not present with other symptoms, is not revealed with standard CT imaging, and is of mortal danger to the patient if untreated. The system can automate interpreting CT scanned images and alert medical personnel about the risk of OCC ligament damage.

In at least one embodiment, the system can include a plugin module to an existing software package, such as an open-source software package called Osirix™. Osirix™ software is a Mac-only based software package that is used primarily for research. The embodiment can use Osirix™ as the interface to the user. Other software packages can be used and the reference to Osirix is only exemplary. In other embodiments, the system can be a stand-alone software package.

Overview

Figure 6:
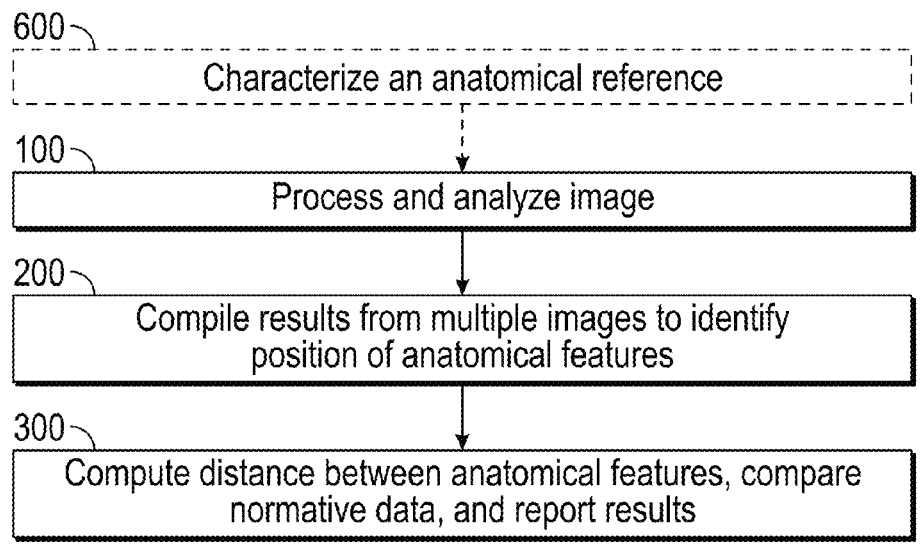
FIG. 6 is an exemplary flowchart of an overview of the method and system of the present disclosure.

FIG. 6 is an exemplary flowchart of an overview of the method and system of the present disclosure. At the highest level, the method and system may be separated into step 100 that processes and analyzes a single CT image; step 200 that compiles the results from the series of images to identify the three-dimensional (3D) position of desired anatomical features such as preselected portions of the basion and dens; and step 300 that computes the anatomical distance, compares that distance with normative data, and reports the results.

Generally, the system, including the software, accepts as input a sequence of images, such as computerized tomography (CT) images, of one or more scanned anatomical regions that contain the preselected anatomical features to be measured. The images can be input as digital images or can be digitized into digital images using procedures known to those with skill in the art. As an example, the images can present sagittal-plane views of the OCC area. If the system is embedded within another software package, such as Osirix™, then the software package may obtain the images and pass the images to the system. In a stand-alone embodiment, these images can be loaded directly from a computer storage, such as a hard drive or other memory device.

An automatic measurement process can be initiated after either the user identifies or the system identifies a starting image to search for relevant anatomical features. In at least one embodiment, the system allows the user to scan to and fro through a series of images to view different sagittal-plane cross-sections to generally locate a first anatomical region of interest having an anatomical reference with at least one of the preselected anatomical features. In other embodiments, the system can automatically search through the images to generally locate the first anatomical region of interest. Known pattern matching methods and systems and other techniques can be used to automatically search the images and to generally find the first anatomical region of interest without user input. Automatic identification of the first anatomical region of interest allows the desired result to be automatically determined without initiation by the user. Then, if a risk is detected from the result, the user can be notified without requesting the measurement.

Once the first anatomical region of interest is located either by the user or automatically, the system with the software can continue the analysis automatically. The system can perform the steps of the analysis, which include searching for the anatomical reference and ultimately the preselected anatomical features and determining the appropriate measurements, comparing to normative data, and reporting the result.

The system can identify the preselected anatomical features in several steps. First, from a preselected first anatomical region in an image, the system can search image pixels in a first direction until the system detects a preselected anatomical reference. The system can then trace in a second direction, which may be different from the first direction, along the anatomical reference until the system detects the position for a first preselected anatomical feature in the current image. The terms "scan", "search", "trace", and "trace line" are used herein broadly to convey the purpose of portions of the digital processing of the image data, realizing that no physical scanner or tracing system that actually moves along the image is required, because the digital processing uses digital data as representing positions, values, and other data that are processed with a program.

From the position of the first preselected anatomical feature, the system searches in a generally predetermined direction, based on expected anatomical structure, for a second anatomical region of interest. The system can use a scanning pattern, such as a V-shaped or L-shaped pattern or other pattern, as it searches for the second anatomical region of interest. Once the second anatomical region of interest is detected, the system can search along a preselected second anatomical reference to determine the position for the second preselected anatomical feature in the current image.

The system also searches other images from an available subset of images to detect in the same way the positions for the first preselected anatomical feature from the individual images and the positions for the second preselected anatomical feature from the individual images.

The positions from the images are compiled and can be mathematically analyzed, so that the most accurate compiled position of the first preselected anatomical feature is determined from the positions found in the individual images. Further, the positions from the images are compiled and can be mathematically analyzed, so that the most accurate composite position of the second preselected anatomical feature is determined from the positions found in the individual images. The compiled position of the second preselected anatomical feature may be on the same image as the compiled position of the first preselected anatomical feature or another image or at some spatially determined position between images.

Once the compiled positions of the first and second anatomical features have been identified, the distance between the features can be determined. The image dimensions and scale are generally either embedded within the image file format, or obtained from other software packages, such as the above referenced Osirix™ software package and others. These values generally include the dimensions of the image pixels, and the distance between the adjacent images. So, with the image and pixel coordinates defined for the positions of the first and second anatomical features, the distance calculation is a geometric computation and advantageously can be calculated in spatial three-dimensions that may traverse across multiple images.

Figure 4:
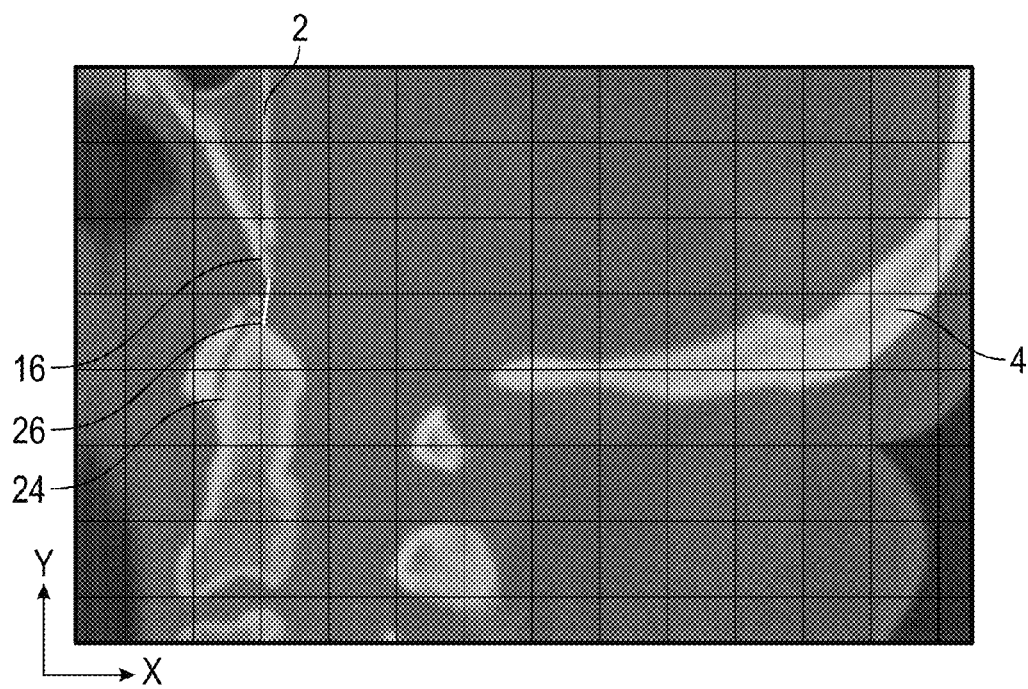
FIG. 4 is a prior art exemplary CT scanned image in a sagittal plane of a typical skull showing anterior and posterior portions of the skull and the basion on the skull located above the dens on the axis.
Figure 5:
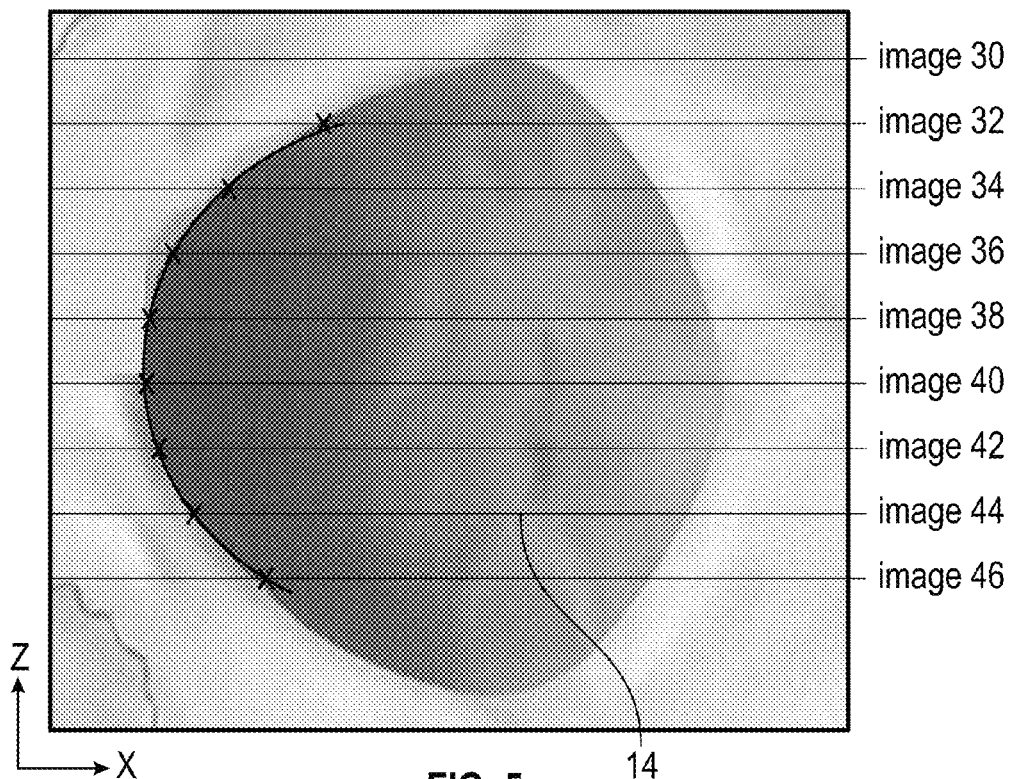
FIG. 5 is a prior art bottom view (anatomical axial view) schematic showing the skull foramen magnum with an edgewise view of sagittal plane images and their positions along the medio-lateral dimension, which images can be used to locate internal anatomical regions and features.

In the example of the OCC measurement for potential ligament damage, saggital-plane cross-sectional images located central to a patient's skull generally show both the skull and vertebrae, such as shown in FIGS. 4 and 5 above. For example, a user or system could locate one of the centrally located images having a first anatomical region of interest as the second cervical vertebra. This second cervical vertebra should be easily identifiable by anyone with basic knowledge of human anatomy. It is not necessary to find the exact central image, but any image showing the second cervical vertebra may suffice. Also, it is not necessary to find the superior portion on the dens, or even the dens itself, just the second cervical vertebra as a starting point to locate ultimately the superior portion of the dens. The system can process the image pixels to find an edge of the bone surface of the second cervical vertebra as an anatomical region of interest, and then trace in a superior direction along the bone surface of the second vertebra to find the dens as an anatomical reference, and then trace along the dens to find the desired anatomical feature, such as the superior portion of the dens in the current image. The system can then search adjacent images to detect, in the same or similar way, the superior portion of the dens in the images. The positions of the superior portion from the plurality of images are compared to find the superior portion of the dens among these images to use for a BDI computation.

From this position, the system can search superiorly in a pattern as the system searches through digital processing for the base of the skull as a second anatomical region of interest. The skull, as an exemplary second anatomical region of interest, should appear in the image as the next bone superior to the dens, because the dens protrudes through and above the first cervical vertebra that is connected with the skull. Once the skull is detected and the bone surface is identified, the system can search through digital processing along the bone surface to find the second anatomical reference, such as the basion, and ultimately the second anatomical feature, the inferior portion of a basion in the current image. Finally, the system searches through digital processing to adjacent images to detect, in the same or similar way, the inferior portion of the basion among the neighboring images. The positions of the inferior portion of the basion from the plurality of images are compared to find the inferior portion of the basion among these images to use for a BDI computation.

Once the positions of the superior portion of the dens and the inferior portion of the basion have been identified, computation of the BDI can be made for example by using three-dimensional spatial calculations. The image dimensions and scale can be embedded within the image file format, or obtained from Osirix or other platform or host program. So, with the image and pixel coordinates defined for the basion and dens, the distance calculation is a simple geometric computation.

In at least one embodiment, the system can be used to search for the dens first and then the basion and in other embodiments, the system can be used to search for the basion first and then the dens.

Various specific strategies have been tested to identify and trace the borders of bones within the CT images. In most cases, the effort is to identify the bone edges throughout the image, which can be quite challenging due to pixel intensity variation, noise, and so forth.

Two strategies, known as "thresholding" and "gradient" strategies, can be used for detecting the anatomical references, such as bone edges in the OCC example. The anatomical reference is then used as a reference surface within the anatomical region to guide the further searching until the desired anatomical feature is more precisely located. A thresholding strategy looks at the actual pixel intensity values of the images, which for CT scans is a reflection of the density of the material that was scanned. These pixel intensity values tend to be higher near the bone edges and on the bone, and lower for non-bone material. An exemplary form of thresholding compares pixel values to some threshold value, and if a pixel is above the threshold, the pixel is considered showing a bone, and if not above the threshold, then the pixel is considered showing a non-bone. The value of the pixel can then be stored and/or processed in the system to guide further the searching or process results. Other pixels can be scanned to indicate bone and non-bone (or other classifications) to guide ultimately the system to identify the position of the desired anatomical features, such as preselected portions of the dens and the basion. Further, the system can provide threshold normalization methods based on the pixel scan results in the image, and on pixel histograms digitally processed from the data, to try and identify a suitable threshold value for each image. While the method works quite well as a practical matter, it is noted that the method can be susceptible to noise and variations in pixel intensities across images, or image sets.

Gradient strategies look at the rate of change of pixel intensities to detect an edge. For example, bone can become non-bone when the pixel intensities change from high to low quickly, and so these strategies look for high gradients. General gradient-based strategies compute the gradient at every pixel, which can be computationally demanding. In at least one embodiment, the system can simplify the computations by computing the gradients in the neighborhood of the search pixel as the system scans looking for bone edges. Also, a centroid-like formula, described below in more detail, can be used that computes not only the magnitude but also the direction of the gradient in the images. The direction also gives an indication of the direction of the bone edge, and thus the direction to continue searching as the system scans along the bone edge as the anatomical reference to locate the preselected anatomical feature.

Having the capability to search along the edge of the bone also facilitates the ability to detect portions of the bone, such as the superior or inferior positions of the bone in an image and in neighboring images. If there is some misalignment during the imaging, the resulting estimation of the BDI should not be substantially affected. Other orientations of the patient for imaging can be used, depending on the selections of the first and second anatomical features.

Advantageously, the system-calculated measurement provides benefits over a manual method of measurement. One advantage is that manual measurement will most always be performed within a single image. The preselected portions of the basion and dens represent anatomical features that are central in the medio-lateral direction, and thus will generally appear within the central image. However, in cases where there is imaging misalignment, joint angulation, or unusual anatomy, the preselected anatomical features may best appear in neighboring images, such as the inferior position of the basion and the superior position of the dens. The system can detect the appropriate image for each anatomical feature and compute the three-dimensional distance between the features properly.

The computed measurement between the anatomical features can be outputted for review. The output can be on printed media or in electronic media. The computed measurement may be reported numerically, graphically, and/or diagrammatically. For the OCC example, the computed BDI and a normative BDI can be displayed in numerical form to the user. For BDI measurements that exceed the threshold, a warning indicator will be displayed to the user suggesting that further examination and careful consideration be given to the possibility of increased risk. In some embodiments, the positions of the anatomical features, such as the preselected portions of the basion and dens, can be graphically indicated for verification. Therefore, if some anomaly in the image were to disrupt the tracing of features and result in erroneous positions, the user will be able to see the flawed result and ignore the analysis.

The sequence of images is recorded at distinct cross-sectional planes, and so there is necessarily some space between consecutive planes that is not clearly imaged. It is reasonable to assume that the selected anatomical features, such as the inferior portion of the basion or superior portion of the dens, may actually occur between planes of the images in the Z-axis referenced above, though adjacent planes may appear to show these portions. Because the system can consider the anatomical geometry in three dimensions, the shapes of the bones across images could be considered and more accurate extrema points estimated by interpolation.

Thus, in one or more embodiments, the system can operate with different levels of automation and regimes:

High level of automation: The system can be simply given a set of images, and it then searches and automatically finds the appropriate bones (anatomical regions, such as the anterior skull and vertebra), the anatomical references (such as the basion and dens), and the appropriate anatomical features (such as the preselected portions of the basion and dens), makes the measurements, compares with normative data, and reports.

Middle level of automation: The user identifies one bone in one image, such as the anterior skull, by clicking the cursor somewhere on that bone or some other method of directing the system to a first bone as an appropriate anatomical region to start. The system then uses the now known location of the first bone to automatically locate the appropriate feature, a second bone as a second region, a second anatomical feature, and then other steps described herein such as making measurements, comparing, and reporting.

Low level of automation: The user identifies the first bone (an anatomical region), an anatomical reference, or even the desired first anatomical feature directly, and the second bone (such as the anterior second vertebra) or even the desired second anatomical feature directly, by indicating to the system each in turn. The system then completes other steps described herein using the known locations of each anatomical region.

While the discussion herein and example below focus on the basion and dens distance for the BDI, other measurements of anatomical features may benefit from the principles taught herein, and some may serve as further indicators for the risk of undetected injury. These may include, for example, the Atlanto-Occipital Interval, or the Lateral Mass Interval, and others. The approach for these other measurements can be similar as the above example for the BDI, using bone edge detection along with feature detection.

EXAMPLE

While the above explanation has been generalized for anatomical features with some discussion of the BDI measurement, the following description provides more details and specific information for the BDI measurement and comparison to normative data for an assessment of the risk for OCC injury. The principles, logic, and considerations, such as starting points in images and stepwise process for directional movements in analyzing pixels, which are provided in this example, can be applied to other sequences and other anatomical features. Thus, the details in this example are only exemplary and not limited to these particular anatomical features, and are explicitly intended to serve as guidelines for other sequences and anatomical features using the teachings herein.

Figure 16:
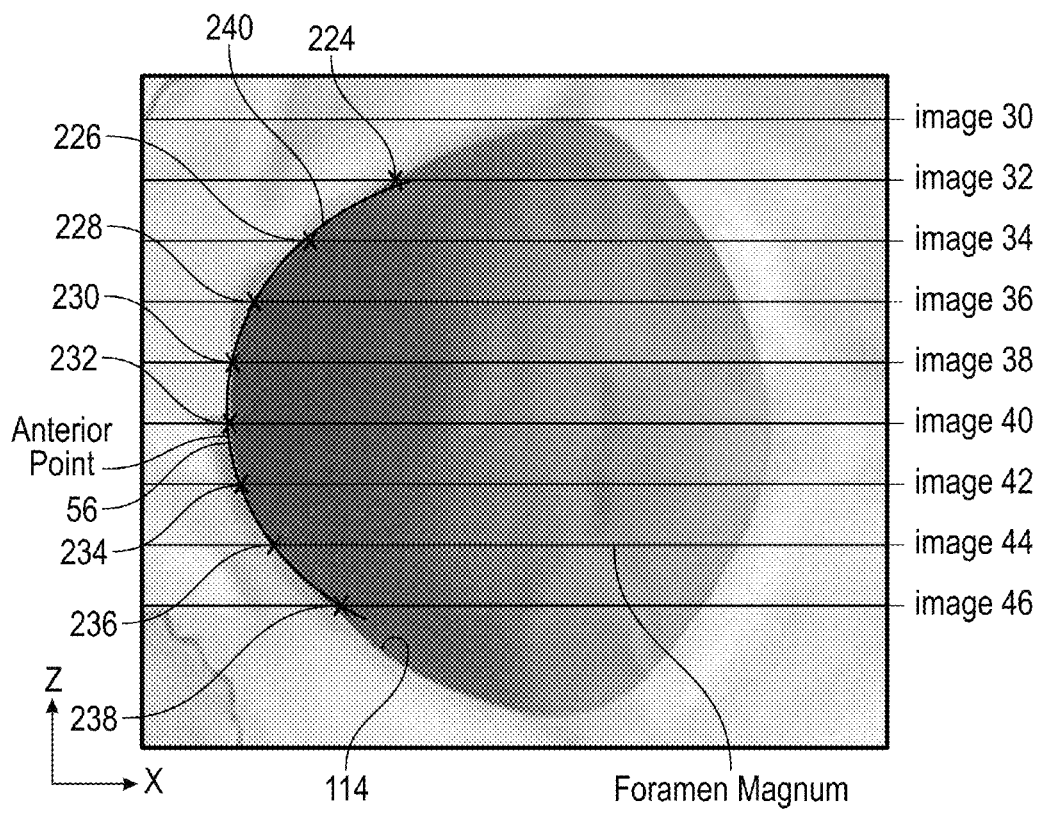
FIG. 16 is a bottom view (anatomical axial view) schematic showing the skull foramen magnum with an edge-wise perspective of sagittal plane images and how anatomical features located in each image are compiled across the medio-lateral dimension to compute the three-dimensional (3D) location of an anatomical feature of interest (e.g., the basion).

Within at least this example, the disclosed system and method, including the software, for determining the BDI accepts as input a series of sagittal-plane CT image files focused on the cervical spine area. It is assumed that these images show the patient in a standard position facing leftward, and that the field of view of the images encompasses at least the inferior (lower) portion of the skull (occipital region) and the entire second vertebra (axis). It is also assumed that sufficient images are included in the series to encompass at least the full medio-lateral span of the axis. For example, positions of a series of sagittal-plane CT image files is illustrated in FIG. 16, described below.

1.0 Overview of Major Steps

As mentioned above and in reference to FIG. 6, the method and system may generally be separated into (1) those steps which process and analyze a single CT image in 2D, labeled as overall step 100; (2) those steps which compile the results from the series of images to identify the three-dimensional (3D) position of the anatomical features, such as preselected portions of the basion and dens, labeled as overall step 200; and (3) those steps that compute the distance between the anatomical features, such as the BDI distance, compare with normative data, and report an estimate of OCC injury risk, labeled as overall step 300. In some embodiments, it may be advantageous to characterize the anatomical reference in step 600. The characterization may facilitate searching and processing the image for the anatomical reference to determine the position of the anatomical feature, and may be illustrated before the step 100. More details are provided in the discussion of FIG. 19 and related figures.

1.1 Major Steps to Analyze a Single CT Image

The steps that may be performed by the disclosed system and method to analyze a single CT image presuppose that the image lies somewhat medially within the sagittal-plane image series, meaning that the foramen magnum (spinal hole of the skull) and the vertebral foramen (spinal hole of the vertebra) should be visible. In a cross-sectional, sagittal-plane view, these anatomical regions (holes) appear as non-bone empty space between either side of the bone material. If these empty spaces are not detected within an image, then the image is assumed not to be anatomically medial, and therefore will not contain the basion or dens.

Figure 7:
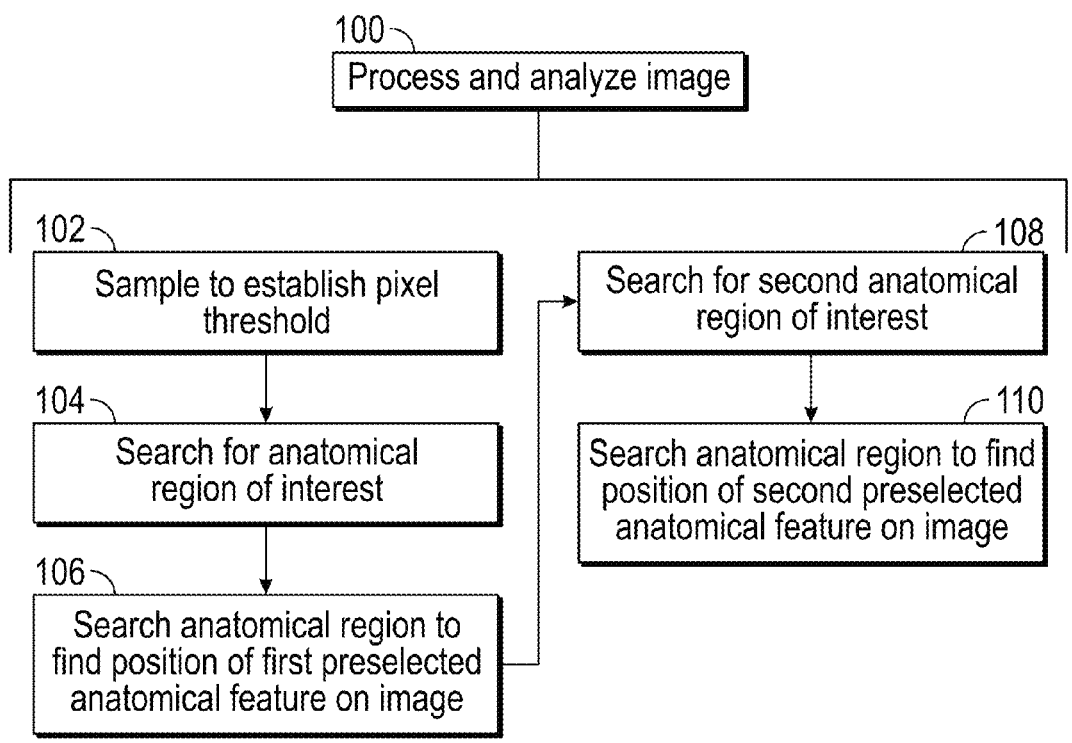
FIG. 7 is an exemplary flowchart expanding on and detailing the steps within FIG. 6 step 100 for processing and analyzing a single image in two dimensions (2D).

FIG. 7 is an exemplary flowchart expanding on and detailing the steps within FIG. 6 step 100 for processing and analyzing a single image in two dimensions (2D). The major steps to analyze a single CT image are listed below followed by a specific reference to a step for the example for the basion and dens determinations. For the steps shown below, as well as all steps disclosed and discussed herein, persons of ordinary skill in the art will understand that, depending on the specific implementation, one or more steps may be combined with one or more other steps, divided into two or more substeps, and/or performed in a different sequence, without departing from the scope of the disclosed embodiments. These major steps include:

Sample to establish pixel threshold; the top region of the image can be sampled to compute a bone/non-bone pixel intensity threshold (step 102);

Search for an anatomical region of interest; the system can automatically search and find the anterior skull near the top of the image (step 104);

Search the anatomical region to find a position of a first preselected anatomical feature on the image; the system can trace along the anterior skull to find the lowest bone portion to establish a best guess of the position of the preselected portion of the basion within the current image (step 106);

Search for a second anatomical region of interest; the system can scan slightly rightward and fully downward to confirm empty space in the image of the vertebral foramen based on typical anatomical relative positions of the basion and the dens (step 108) to find the second vertebra (axis); and Search the second anatomical region to find position of the second reference and the preselected second anatomical feature on the image; as the downward search occurs, search leftward to detect bone material of the second vertebra and trace along the second vertebra to find the dens and then the superior point of the dens to establish a best guess of the position of the preselected portion of the dens within the current image (step 110).

The information gathered for the positions of the best guesses of the preselected portions of the basion and the dens can be recorded for each processed image and used for subsequent comparisons between the processed images, as described below, to result in the determined position of each anatomical feature.

1.2 Major Steps to Analyze the Series of CT Images

The steps performed by the disclosed system and method to analyze the series of CT images as a composite presuppose that at least some number of images have been processed to find within each image at least the image positions of the first and second anatomical features. For the basion and dens determination, the steps to analyze the series of CT images presuppose that at least some number of images have been processed to find within each image (1) the top right position of the anterior skull, (2) a basion position estimate, (3) show that the vertebral foramen is present, and (4) a dens position estimate. The data across several images as a composite are then processed by the disclosed system and method to identify which image contains the best estimate for the position for the 3D basion position, and which image contains the best estimate for the position of the 3D dens position.

Figure 15:
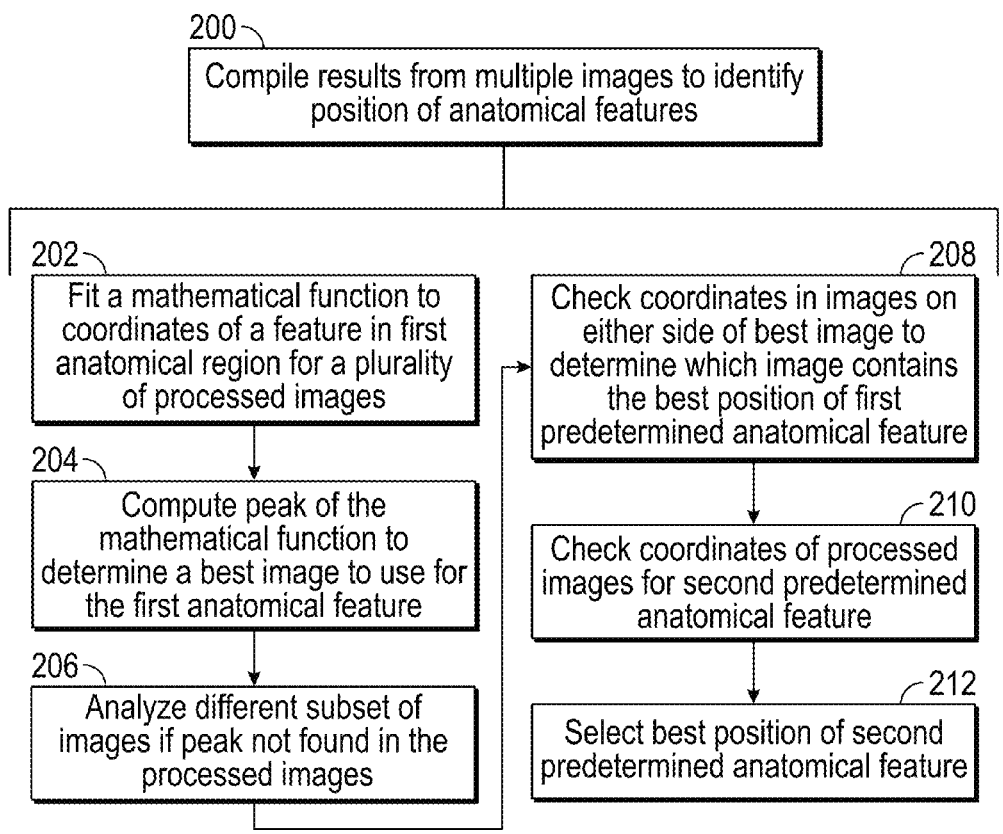
FIG. 15 is an exemplary flowchart expanding on and detailing the steps within FIG. 6 step 200, for compiling results from multiple images to identify the three-dimensional location of anatomical features of interest.

FIG. 15 is an exemplary flowchart expanding on and detailing the steps within FIG. 6 step 200, for compiling results from multiple images to identify the three-dimensional location of anatomical features of interest. The major steps to analyze the series of CT images are listed below with specific reference to the example for the basion and dens determinations:

Fit a mathematical function to the coordinates along at least one axis of a feature in the first anatomical region for a plurality of the processed images; in at least one embodiment, the system can fit a quadratic polynomial function to the horizontal X-axis coordinates of the top anterior skull as a convenient reference to approximate the basion position and to select a subset of images for compiling to select the compiled basion position in a later step; in at least one other embodiment, the system can directly use the position of the basion from each processed image to fit the mathematical function (step 202);

Compute a peak of the mathematical function to determine a best image to use for the position of the first anatomical feature; the system can compute the quadratic peak of the polynomial and determine the best image having a horizontal X-axis coordinate of the top anterior skull as a reference feature that is closest to the peak to then use as the best image for the compiled position of the basion (step 204);

Analyze a different subset of images if the peak from the mathematical function is not found in the processed images; the system can recurse and process a different subset of the series of scanned images if the peak is not found within the processed images (step 206);

Check images on either side of the best image to determine which image contains the best compiled position for the first predetermined anatomical feature that can minimize the computed distance from the second predetermined anatomical feature; the system can check images on either side of the best image to find which contains the best position of the preselected portion of the basion, which for this particular anatomical structure will be the inferior portion of the basion (that is, the portion at the minimum vertical Y-axis coordinate the inferior) (step 208); and Search the processed images for the second predetermined anatomical feature and select a best position of the second predetermined anatomical feature; the system can accommodate a wide surface of an anatomical feature such as a preselected portion of the dens by searching multiple dens digital coordinates across multiple processed images to identify a rise, plateau, and fall in a vertical direction and computing the center image of the plateau region as that best image containing the position of second preselected anatomical feature (step 210).

1.3 Major Steps to Interpret BDI Results

Figure 18:
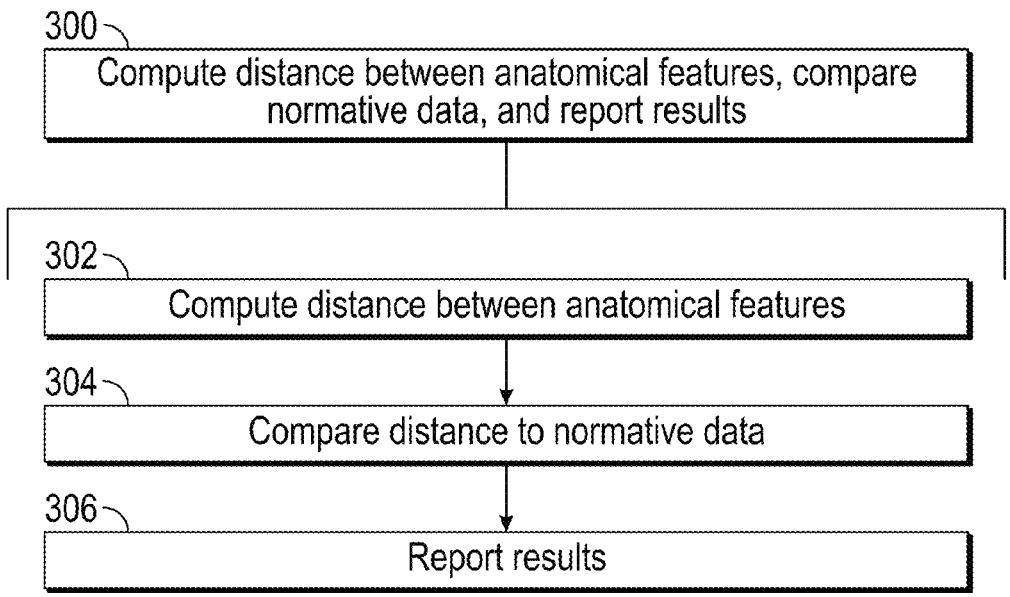
FIG. 18 is an exemplary flowchart expanding on and detailing the steps within FIG. 6 step 300 for computing the distance between the first and second preselected anatomical features, comparing to normative date, and reporting the results from the flowchart of FIG. 6.

FIG. 18 is an exemplary flowchart of detailed steps performed by the disclosed system and method for the step 300 of computing the distance between the first and second preselected anatomical features, comparing to normative date, and reporting the results from the flowchart of FIG. 6. The major steps to compute the distance, compare, and report are listed below with specific reference to the example for the basion and dens determinations:

Compute a distance between the first and second preselected anatomical features; the system can compute a distance between the identified positions of the preselected portions of the basion and the dens (BDI) (step 302);

Compare the computed distance to normative data; the system can compare the computed distance for the BDI to normative data that indicates a BDI threshold for injury (step 304); and Report results; the system can report the BDI comparison as an assessment of OCC injury risk (step 306).

Having described the flowcharts and associated steps, further details of the steps performed by the disclosed system and method are provided below with reference to the subject matter in each enumerated step for at least one embodiment.

2.0 Details for Processing and Analyzing Individual CT Images in Step 100

The system and method disclosed herein is capable of processing raw image data in a number of well-known formats. In some embodiments, the raw image data may be in the form of a plurality of pixels represented by a one-dimensional (1D) vector or array of integer values, each integer value representing image intensity at each pixel. Pixel intensity values are typically between 0 and 255 for an 8-bit pixel, 0 and 4095 for a 12-bit pixel, and so forth. Each pixel represents a two-dimensional (2D) position in the image, and has an X-(horizontal) and Y-(vertical) coordinate along an X and Y axis. The 2D arrangement of pixels is organized into the 1D vector by sequentially ordering each pixel row of intensity values one after the other. Thus, the method and system can quickly and easily obtain the pixel value for any (X,Y) coordinate in the image. Further, the depth of each image is known relative to each other from the scanning process and thus a Z-coordinate along a Z-axis can be established relative to each image to compute three-dimensional ("3D") positions of regions, features, and other structures within the set of images.

To reduce processing time that otherwise would occur if all available images were processed and then compiled, the system can begin with the numbered image of the available images along the Z-axis where the expected location of the preselected anatomical feature(s) will be found, and several on either side of the image by image number to form a subset of images for processing. For example in the OCC discussion regarding FIG. 5, the middle image 40 of a set of sagittal-plane images might be selected along with images 30-38 and 42-48 to form an initial subset of images even though in actuality additional sagittal-plane images (not shown) might be available. In at least one embodiment, a subset of the series of images corresponding to the middle sagittal-plane image and four adjacent images on either side in the Z-axis direction (laterally) are loaded and processed initially.

2.1 Compute a Bone/Non-Bone Pixel Intensity Threshold in Step 102

The objective of this step is to compute a pixel intensity value that represents a distinguishing level between pixels representing bone and those not representing bone. Bone material appears brighter in the images, and thus has higher pixel intensity values. Preferably, the threshold will lie somewhere mid-range between the higher bone pixel intensities and the lower non-bone pixel intensities. Once the threshold is computed for a given image, pixels on the given image with intensities above the threshold are taken as bone, and those below the threshold are taken as not bone. In general, the method and system identifies the lowest pixel intensity of the largest number of pixels that are not blank pixels (that is, pixels with no image information), and selects a pixel intensity that is more than the lowest pixel intensity of the largest number of pixels to represent a pixel intensity of a bone (or a pixel intensity that is less than the lowest pixel intensity of the largest number of pixels to represent a pixel intensity of a non-bone).

2.1.1 Identify Top of Image Content

In many cases, an image may contain rows of blank pixels, that is, pixels that do not actually contain any CT image information, but instead are just dark. The method and system attempts to filter out these pixels, and so the first step is to find where the actual image data begins. The method and system searches a top row of the image and determines the maximum (max) and minimum (min) pixel intensities within the row. If the max and min are equivalent, or if the max is a low value (e.g., 10), the row is assumed to not contain real data. The method and system continues searching downward row by row, generally starting with the top, until a row with real data is found. Subsequent searching will begin from this row (Y coordinate.

2.1.2 Compute Histogram of Top Image Region

The threshold will be computed based on pixel values observed in the top region of the image where both skull bone material and non-bone material is assumed to appear. The purpose of the current step is to characterize the pixels in this region of the image, so a threshold can be computed.

First, a pixel region of the image is defined to include the top 1 centimeter (cm), as an example, of pixel rows. Because the raw image format includes the physical dimension of each image, the number of pixels in a cm is readily obtained. Next, a pixel intensity histogram of this region is constructed, which could be accomplished by typical means known in the art, or by means intended to enhance speed of processing. In at least one embodiment, for example, this region of the image is scanned left to right, and the maximum pixel intensity within each column of pixels is recorded in a data vector, that is, the maximum pixel intensity within a small window 1 pixel wide and 1 cm tall is computed, and such is done for each column left to right across the entire image. While the example can use a 1 pixel×1 cm window, other window sizes have been tested and can be used if needed (e.g., a window of 4 pixels wide and 2 cm high). However, the 1 pixel×1 cm window has been experimentally found to be both effective and speedy.

Figure 8:
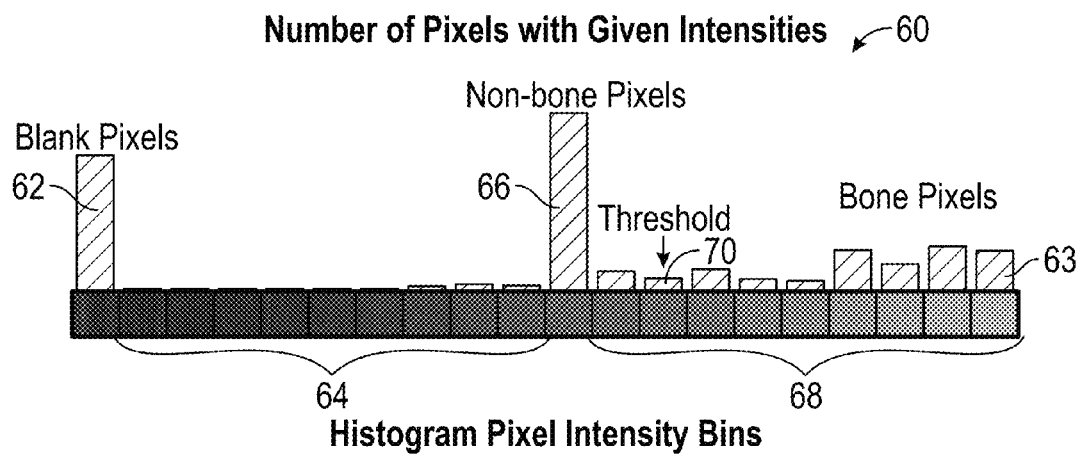
FIG. 8 is an exemplary histogram of pixel analysis for establishing a pixel intensity threshold to distinguish bone from non-bone for a given image according to the disclosure.

FIG. 8 is an exemplary histogram of pixel analysis for establishing a pixel intensity threshold to distinguish bone from non-bone for a given image according to the disclosure. A histogram 60 is computed from the vector of maximum pixel intensities. As a non-limiting example, the histogram has twenty bins, with the first bin 62 representing the number of pixels with lowest intensities (e.g., nearly zero), and the last bin 63 representing the number of pixels with the highest intensities (e.g., that of the max pixel intensity in the evaluated region). For example, if the pixel intensities in the vector vary from an assigned value of 0 to 1000, then the first bin 62 could hold the count of pixels with intensities from 0 to 50, the next bin could the count of pixels from 51 to 100, and so on to bin 63 that holds the count of pixels from 951 to 1000. The number of bins for the histogram dimension is not that critical, but experimentally 20 bins seem to be effective. Because there will be greyer areas (non-bone) and whiter areas (bone) within the region, the histogram will generally form at least one hump representing large numbers of pixels in the greyer bins and/or large numbers in the whiter bins. Occasionally, the left and right portion of the image may contain blank pixels (black), which will form another hump at the very beginning (or left end) of the histogram.

2.1.3 Compute the Bone/Non-Bone Pixel Intensity Threshold

The histogram data is used to compute an appropriate threshold value by identifying the first big hump 66 in the histogram 60 past the very beginning bins. This hump represents large numbers of non-bone pixels, and so the threshold should be above the intensity values of these pixels. This hump 66 is found by first scanning all the bins of the histogram to find the maximum count in any one bin. As an example, a hump is assumed to have a count of at least half of the total count of the maximum bin. Then, starting from the left bin, the first bin with at least half the maximum count is found (after skipping over the first one or two bins that contains the blank pixels) to establish a left edge of the hump. The right edge of the hump is found by checking the adjacent bins to the right until the count in the particular bin falls below half of the count of the maximum bin. Non-bone pixels 64 are generally within or to the left of the hump 66 and bone pixels are generally to the right of the hump 66.

As an example, the pixel threshold can be defined as that pixel intensity corresponding to the pixels in the bin two positions above that of the right edge of the first hump. The value of two positions above the right edge of the first hump is experimentally effective to better ensure that bone pixels are being used in the searching functions along bone structures described herein. That is, if the first hump is found in bin 66, then the pixel intensity (or average pixel intensities) of pixels in bin 70 is taken as the threshold. In other embodiments, more or less than two bins above the hump can be used to define the threshold.

With the threshold established, the system can search and analyze the pixels in the image.

2.2 Find Anatomical Region of Interest in Step 104

Figure 9:
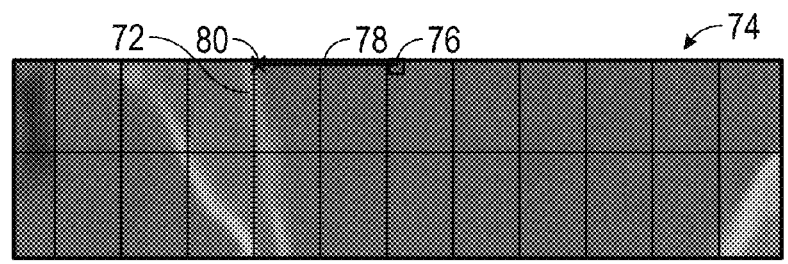
FIG. 9 is an exemplary image with an anterior portion of the skull, a posterior portion of the skull, and a trace line illustrating digital processing of the image in locating the desired anatomical region of interest.

FIG. 9 is an exemplary image with an anterior portion of the skull, a posterior portion of the skull, and a trace line illustrating digital processing of the image in locating the desired anatomical region of interest. The aim of this step is to find an anatomical region of interest in the images from which a further search for an anatomical reference and a preselected anatomical feature can be made. For example, this step can find the right edge of the anterior portion of the skull as an anatomical region of interest 72 on or within which is an anatomical reference of interest, such as the basion 16. The anatomical region of interest can be an anatomical structure, such as a bone, or if sufficiently specific, then, a general area in proximity to an anatomical reference for the preselected anatomical feature. The search can start at the top of a given image 74 being processed. This right edge of the anterior portion of the skull should lie somewhat left of middle in the image if the patient is facing left. Starting with the middle pixel 76 at the top of the image, the following steps can be applied:

If the pixel 76 is below the threshold, search in a direction 78 to the left until a pixel 80 is found above the threshold to indicate bone;

If the pixel 76 is above the threshold, search in a direction 78 to the right until a pixel is found not above the threshold; then back up one pixel to the left to return to a bone pixel.

2.3 Search Anatomical Region for Position of First Preselected Anatomical Feature on the Image in Step 106

The aim of this step is to search the anatomical region of interest for the anatomical reference and ultimately the position of the first preselected anatomical feature in a current image. For the basion example, the search can be made by tracing around the right edge of the anterior skull bone section to find the basion and then the position of the inferior portion of the basion for the current image. In at least one embodiment, the searching can advantageously be done in clockwise increments, because the particular exemplary anatomical feature is below the starting position of the anterior skull bone section and because the starting position is on the right portion of the anterior skull bone section. Other anatomical structures and position could reverse the direction and the clock-wise to counter-clockwise rotational increments.

Starting with the top-right position of the anterior skull bone appearing in the image, the method and system tracks the boundary between those pixels above and those pixels below the threshold until it finds the lowest Y-coordinate of the bone structure, which is assumed to be the best guess for the preselected anatomical feature, such as the inferior portion of the basion in this image.

The searching to trace begins at a pixel within and at the right edge of a bone. The searching digitally "peeks" at adjacent pixels by previewing one or more selected characteristics of the adjacent pixel and digitally steps to that pixel only if the adjacent pixel is also within bone (above the threshold intensity). In other words, the system can process the pixel with a coordinate that is adjacent to the current pixel to determine if the pixel is also within bone that would therefore be above the threshold intensity and mathematically indexes to that pixel if such pixel meets the threshold value. The system peeks in one of the four coordinate directions, beginning with the right direction. If a peek lands within bone, the system steps to that pixel, and rotates the peek direction 90 degrees counter-clockwise (CCW). If a peek lands in a pixel below the threshold (non-bone), the system remains at the current pixel (does not step), and rotates the peek direction 90 degrees clockwise (CW). This process continues until some criterion is met, such as reaching a lowest portion of bone in the Y-axis direction, which is assumed to be the inferior portion of the basion in this example.

Figure 10:
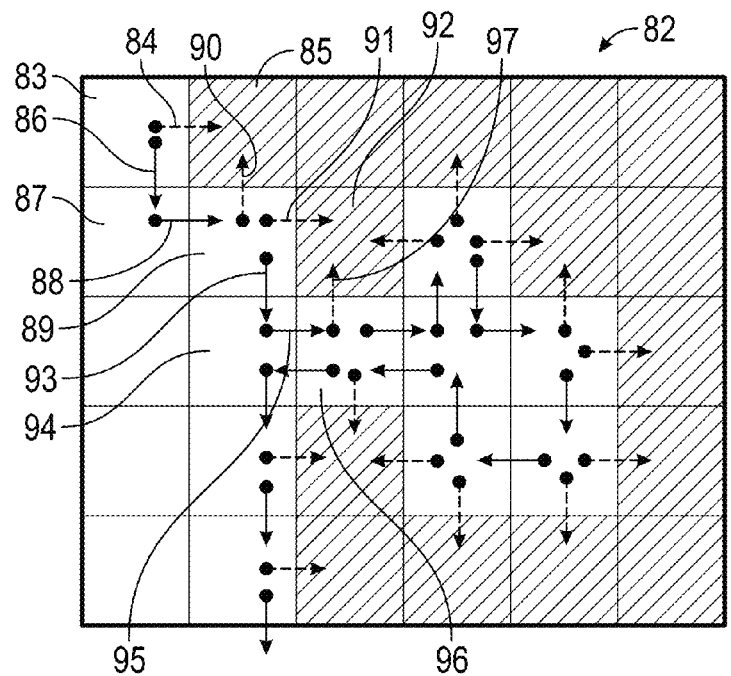
FIG. 10 is an exemplary search sequence tracing pixel by pixel along a bone surface of a hypothetical region of interest.

FIG. 10 is an exemplary search sequence tracing pixel by pixel along a bone surface within a hypothetical region of interest. A small, hypothetical region 82 includes bone and non-bone pixels (each pixel being represented by a light or dark square, and outlined with a grey rectangle). In this example, the system begins in the upper left pixel 83, with a peek direction 84 to the right. The first peek (pink arrow) lands in a pixel 85 that is below the threshold (dark color), so a 90 degrees CW turn sets the peek direction 86 to down. That peek direction 86 lands in a pixel 87 that is above the threshold (light color), and so the system increments (green arrow) to pixel 87 and the peek direction 88 is turned 90 degrees CCW back to the right. The rightward peek direction 88 lands in a pixel 89 above the threshold, so the system increments (green arrow) to pixel 89 and the peek direction 90 is turned CCW to up. The up peek (pink arrow) lands in the pixel 85 that is below the threshold, so the peek direction 91 is turned CW to the right. The peek direction 91 lands in a pixel 92 that is below the threshold, so the peek direction 93 is turned CW again to down. The down peek direction 93 lands in a pixel 94 that is above the threshold and so the system increments to pixel 94, and the peek direction 95 is turned CCW to the right. The right peek direction 95 lands in a pixel above the threshold and the system increments to pixel 96. This process is continued all the way around until the pixel tracing exits the hypothetical image region.

Figure 2:
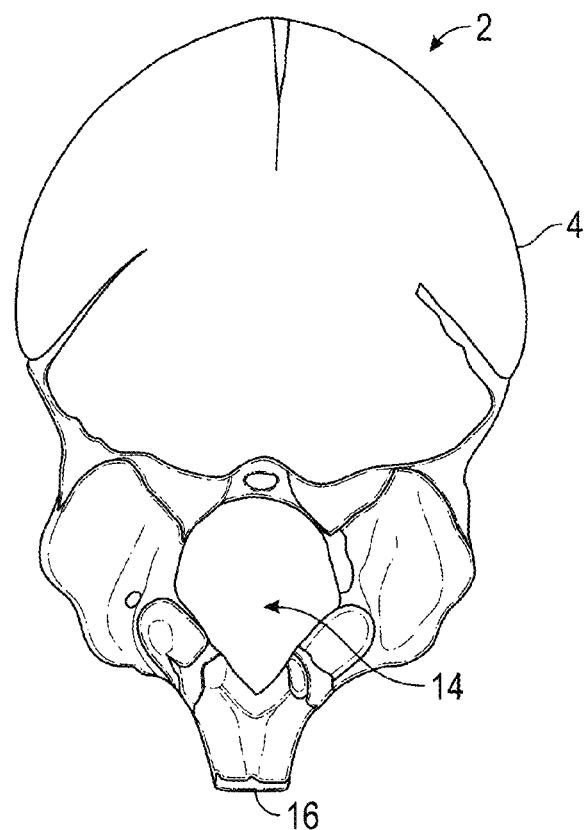
FIG. 2 is a prior art drawing of an inferior view of the bottom of the skull showing the basion and foramen magnum.
Figure 11:
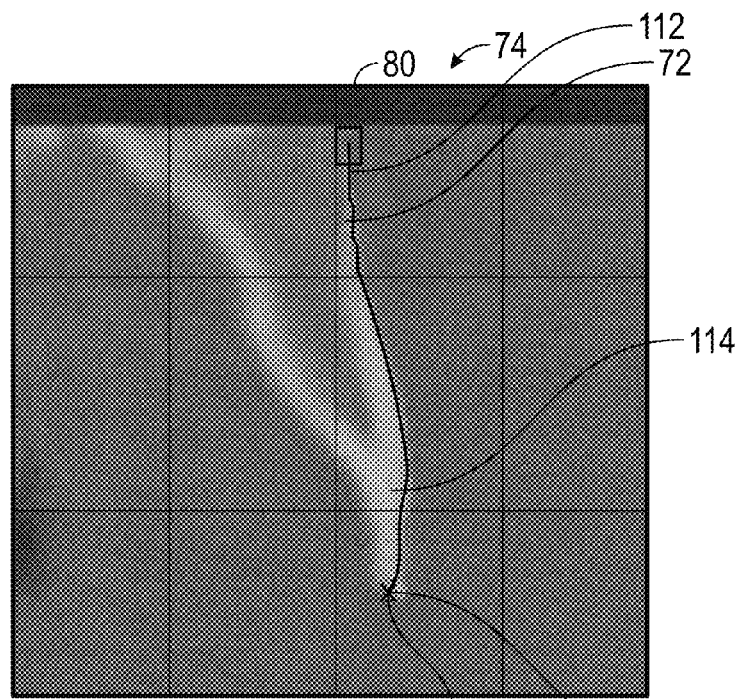
FIG. 11 is an exemplary image of an anterior portion of the skull, with a line illustrating digital processing of the image tracing along the bone surface to identify the first preselected anatomical feature in the current image, such as the inferior portion of the basion in the image.

FIG. 11 is an exemplary image of an anterior portion of the skull, with a line illustrating digital processing of the image tracing along the bone surface to identify the first preselected anatomical feature in the current image, such as the inferior portion of the basion in the image. Note that the top several rows in this picture are blank (dark) and can be skipped by the processing. Note also that grey grid lines have been overlain on the image for visual reference, but are not part of the image data, and are not processed by the algorithm. The figure shows the tracing for the CT image 74 of the anterior portion of the lower skull. The searching traces along the edge of the anterior portion of the bone of the anatomical region 72 at the bone pixel 80 in a downward direction 112 to the anatomical reference 114 to a position 116 of the preselected anatomical feature 134, such as the inferior portion of the basion 16 in FIG. 2, as viewed from the current image.

To find the basion, an exemplary criterion is that the trace reaches a point of a minimum Y-axis coordinate (an inferior position) along the identified bone structure having the preselected anatomical feature. This criterion is detected by tracking the minimum Y-axis coordinate at each increment of pixels along the trace. So long as the trace is moving downward, the minimum Y-axis coordinate continues to be updated. It has been experimentally found that if six consecutive steps are taken without hitting a new minimum Y-axis coordinate, it can be assumed that the lowest pixel has been reached, although other numbers can be used. Another criteria can be the amount of steps equivalent to a measured distance, for example 5 millimeters, without finding a new minimum Y-axis coordinate. The last pixel traced that was a new minimum Y-axis is deemed to be the position 116 of the basion for the current image, as an example.

2.4 Search for Second Anatomical Region of Interest in Step 108

2.4.1 Confirm Non-Bone Space of Vertebral Foramen

Figure 3:
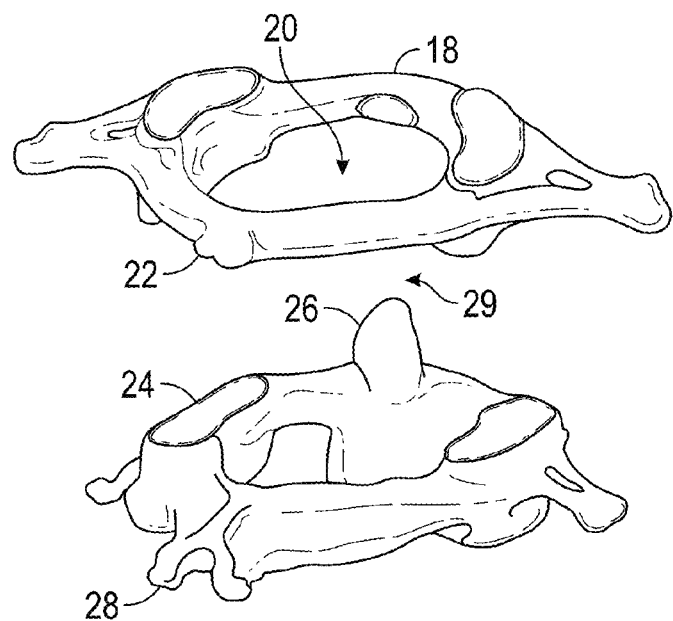
FIG. 3 is a prior art perspective drawing of a first vertebra ("atlas") located above a second vertebra ("axis") with a dens and a vertebral foramen.

This step searches downward from the position of the first preselected anatomical feature 134 shown in FIG. 11 (such as most inferior portion of the basion 16 shown in FIG. 2) in the current image to find the non-bone space formed by the vertebral foramen 20, shown in FIG. 3. Images in which the vertebral foramen appear are assumed to be medial in the anatomy, and so are good candidates for containing the true basion and dens positions.

Figure 12:
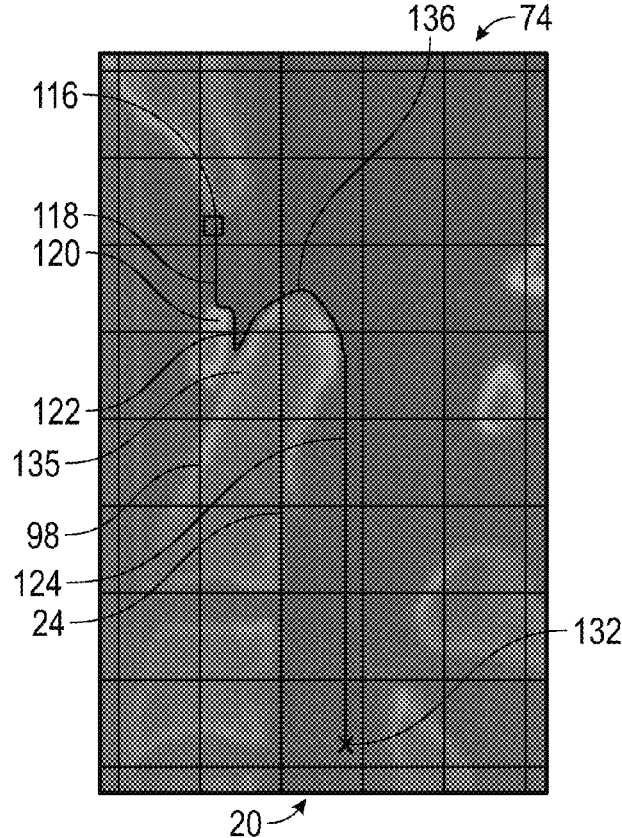
FIG. 12 is an exemplary image of an anterior portion of the skull, with a line illustrating digital processing of the image tracing downward for a second anatomical region of interest.

FIG. 12 is an exemplary image of an anterior portion of the skull, with a line illustrating digital processing of the image tracing downward for a second anatomical region of interest 98. Using the example of the preselected portions of the basion and dens as preselected anatomical features, the system traces vertically in a downward direction 118 from the image position 116 in the current image 74, searching for any pixel above the threshold, that is, a bone pixel. The bone pixel can represent a bone of the second vertebra, as an exemplary second anatomical region of interest 98. The second vertebra will include the dens, as an exemplary second anatomical reference 135 having a second preselected anatomical feature 136 as the most superior point on the dens. The tracing continues downward for a vertical distance of up to 6 cm, with the assumption that 6 cm is a sufficient distance to find bone if the tracing is not within the vertebral foramen 20. If bone is detected during a vertical trace, such as bone pixel 120, then a new vertical trace is initiated from the image position 116, but one pixel to the right. If bone is detected again, such as bone pixel 120, then a new vertical trace is initiated one more pixel to the right. This process is continued until either 1) a full 6 cm vertical trace is completed without finding bone, or 2) the next new vertical trace would be initiated at more than 2 cm right of the original image position 116. It is assumed that vertebral foramen 20 would be found within 2 cm right of the basion at position 116, so anatomically for this example, it is believed that there is no need to search beyond that distance to the right. In FIG. 12, the search begins at the position 116, and a trace line 122 represents where each vertical trace ended, until the last vertical trace at line 124 succeeds in reaching a full 6 cm at the pixel 132, identified in FIG. 12 as an "X".

2.4.2 Find Bone Material of Axis

Figure 13:
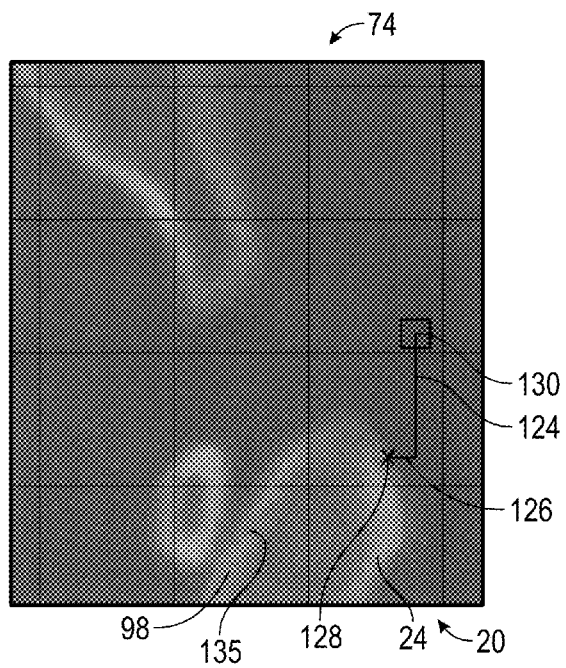
FIG. 13 is an exemplary image of an anterior portion of the skull and axis, with a line illustrating digital processing of the image tracing for a second anatomical region of interest.

FIG. 13 is an exemplary image of an anterior portion of the skull and axis, with a line illustrating digital processing of the image tracing for a second anatomical reference.

FIG. 13 is an exemplary image of an anterior portion of the skull and axis, with a line illustrating digital processing of the image tracing for the second anatomical region of interest 98. Having found the vertebral foramen 20, and the X-axis coordinate at which a vertical drop into the vertebral foramen can occur, the next step is to find any portion on the right edge of the anatomical region of interest 98, which for example, can be the second cervical vertebra (axis) 24, also shown in FIG. 3. It is assumed that the axis 24 will be the highest bone nearest the vertical line 124 that traces into the vertebral foramen 20. So, for this step, the system traces down that the vertical line 124 and can start at a pixel 130 having a Y-axis coordinate that corresponds to the Y-axis coordinate of position 116 that has been shifted over to the X-axis coordinate of the vertical line 124. Along each downward Y-axis coordinate of a pixel, the system can peek along the direction 126 up to 0.25 cm to find any pixel with an intensity above the threshold (that is, within bone), such as bone pixel 128. If found, that pixel is taken to be a position on the axis bone 24.

2.5 Search Anatomical Region for Position of Second Preselected Anatomical Feature on the Image in Step 110

Figure 14:
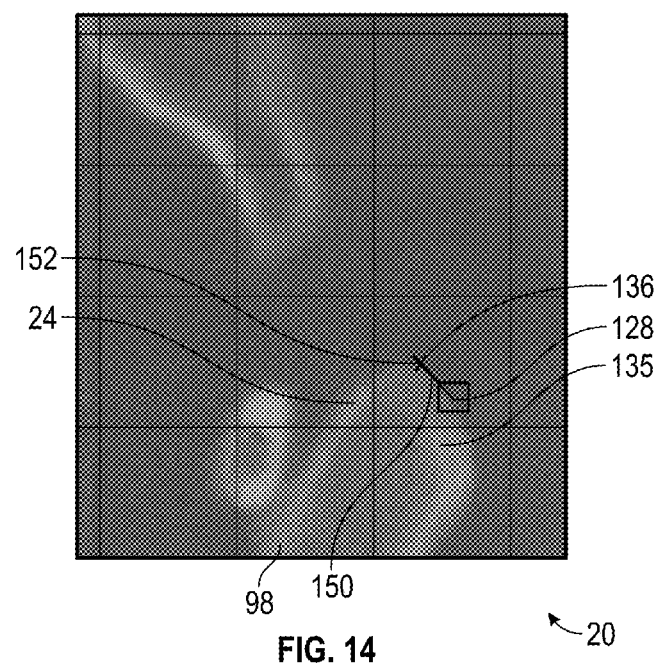
FIG. 14 is an exemplary image of an anterior portion of the skull and axis, with a line illustrating digital processing of the image tracing along a bone surface to identify the second anatomical reference and ultimately the second preselected anatomical feature in the current image.

FIG. 14 is an exemplary image of an anterior portion of the skull and axis, with a line illustrating digital processing of the image tracing along a bone surface to identify the second anatomical reference and ultimately the second preselected anatomical feature in the current image. The aim of this step is to search the second anatomical reference 135 and ultimately the position of the second preselected anatomical feature 136 in the current image being processed. For the basion-dens example, having found a bone pixel 128 on the right edge of the axis 24, the next step is to trace counterclockwise (CCW) around the bone contour in an upward direction to find the dens 26 (shown on FIG. 3).*and* then the most superior portion of the dens, which is taken to be the best guess for the position of the superior portion of the dens 26 as the second preselected anatomical feature 136.

The process for such tracing is similar as for tracing clockwise (CW) to find the basion described above and particularly in FIG. 10, except that search direction rotations are reversed, due to the overall direction being upward along the indicated side of the skull. The system peeks at adjacent pixels and steps only if the adjacent pixel is within bone. The system begins with a rightward peek direction. If a peek lands within a bone pixel above the threshold established above, the system increments to that pixel, and rotates the peek direction 90 degrees CW. If a peek lands in a non-bone pixel, the system does not increment, but rotates the peek direction 90 degrees CCW. This process is continued until a maximum Y-axis coordinate is found that is not exceeded for at least six subsequent steps. The maximum Y-axis coordinate is deemed to be the image position 152 of the second anatomical feature 136, such as the superior portion of the dens 26 (shown in FIG. 3), for the current image.

3.0 Details for Compiling Results from a Series of CT Images in Step 200

In this step, the system accepts as input the processed subset of sagittal-plane images of the occipital-cervical area. In some embodiments, the actual coordinates of the first preselected anatomical feature, such as the inferior portion of the basion, in each processed image as determined above can be used to determine the compiled position of the feature from the several images that would represent the most accurate 3D position.

Analysis of the series of CT Images proceeds with the assumption that the subset of individual images has been processed, and that each shows the vertebral foramen (i.e., that each is medially located), and that for each the basion, dens, and top right edge portion of the skull (at or near the top of the image) have been found. The objective of the subset image analysis is to determine which image contains the best estimate for the 3D basion position, and which contains the best estimate for the 3D dens position. Therefore, a key variable is the image number, which both indexes a specific cross-sectional image and spatially refers to a medio-lateral depth dimension (as a Z-axis coordinate) implicit in the image series.

3.1 Fit a Mathematical Function for a Feature in the First Anatomical Region in Step 202

Some mathematical filtering can be done to confirm that the appropriate subset of images has been processed that would likely have the best data for the 3D positions of the preselected anatomical features. The filtering can use an anatomical region that may or may not be the same as the preselected anatomical region. In the basion-dens example, an anatomical region can be the top anterior skull portion in each image that is initially located in the searching for bone pixel 80, as described in relation to FIG. 9. (In other examples, the anatomical region could be the second vertebra for the dens.) For such an example, the system can locate the inner surface of the skull on the anterior side. Because of the skull's roundedness, the horizontal position (X-axis coordinate) of this position varies across successive images. Specifically, in midline sagittal-plane images, this portion will appear more anterior than in images that are located more laterally to either side in the Z-axis direction.

The system can use an anatomical region to expeditiously locate a mid-line image by finding where the top portion is most anterior. To do so, the system can just scan back and forth across the images to find the one containing the most anterior portion. But, it may occur that the most anterior portion lies outside of the set of images initially selected for processing. To address this possibility, the system can fit a mathematical function, such as a quadratic function to the values of the X- and Z-axis coordinates of this top portion, of the form: (X-axis coordinate)=$a*$(Z-axis coordinate)$^2$+$b*$(Z-axis coordinate)+$c$. Given several points, the coefficients of the quadratic can be determined by standard means. The quadratic function can then be analyzed to identify which image should contain the most anterior portion, and if that image is within the set of images already processed.

FIG. 16 is a bottom view (anatomical axial view) schematic showing the skull foramen magnum with an edge-wise perspective of sagittal plane images and how portions of an anatomical region located in each image are compiled across the medio-lateral dimension to compute the three-dimensional (3D) location of a preselected anatomical feature, such as the inferior portion of the basion. In FIG. 16, the mathematical function fits a curve 240 using points 224-238 for the adjacent exemplary images 30-46 to calculate the location of the most anterior portion of the anatomical region in three-dimensions, which is the foramen magnum in this example. Note that in FIG. 16, the rim of the foramen magnum 14 is traced, but in practice, the system can use the same approach to trace coordinates along the inner surface of the skull where it intersects the top of the image as shown for example in the image of FIG. 9. The most anterior portion of the rounded shape of either anatomical region could act as a general locating guide of the basion and/or dens. Thus, FIG. 16 is illustrative of the concept, realizing that various anatomical regions could be selected. In this example, the curve 240 is generated by finding a mathematical formula to best fit the points of intersection of the portions of the anatomical region, such as the foramen magnum, in the X-axis with the sagittal-plane images in the Z-axis.

3.2 Determine Best Image Having Predetermined Anatomical Feature in Step 204

A good first estimate of the location of the midline, and thus the appropriate 3D position of the preselected portion of the basion (or other anatomical feature), can be found where the X-axis coordinate of the top anterior skull is most anterior (or the foramen magnum in FIG. 16 above). For example, the system can use the extreme of the quadratic function of a curve 240 to estimate which image contains the most anterior portion. The extreme of a quadratic function is easily obtained by differentiating and setting the result equal to zero. The Z-axis coordinate obtained from this calculation correlates to the image at which the X-axis coordinate reaches an extreme. If the X-axis coordinate extreme is a minimum (as expected), then it means the portion is most anterior (to the left in a leftward-facing patient). However, if the extreme is not a minimum, or if the Z-axis coordinate of the extreme lies outside the subset of images analyzed, then the subset of images is assumed to not include the image of the desired 3D position of the preselected portion of the basion, and so the subset of images is expanded or revised.

3.3 Analyze Different Subset of Images in Step 206

Figure 17:
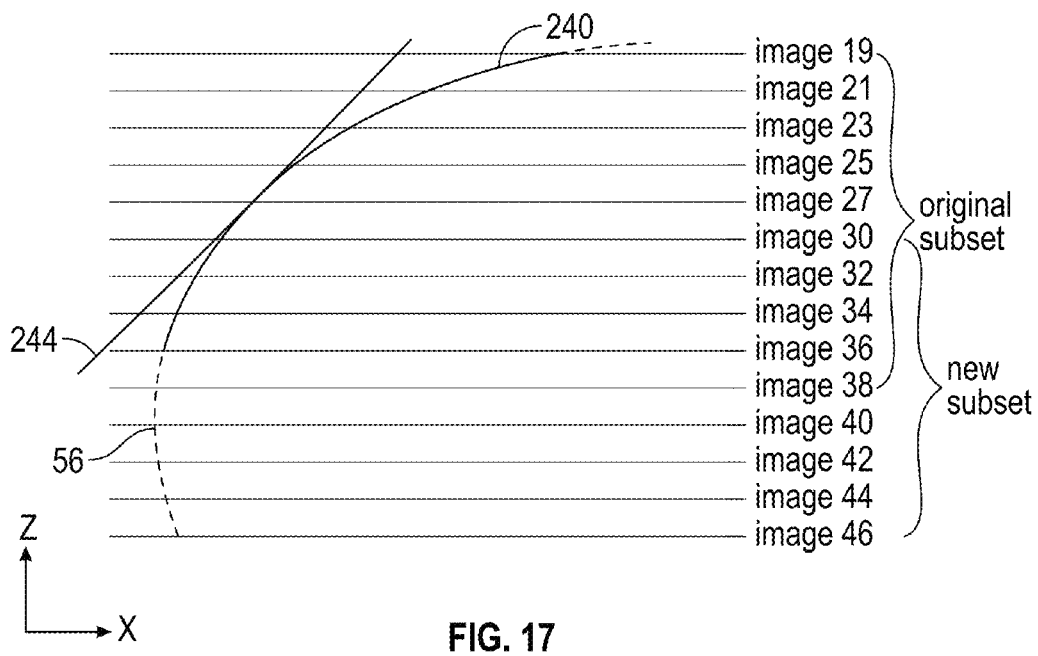
FIG. 17 is a chart showing a mathematical correlation of a subset of images to the slope of the superimposed curve on the anterior portion of the skull to confirm proper images in the subset.

FIG. 17 is a chart graphing (red line) the locations (e.g., X-coordinates) of portions of an anatomical region identified in a hypothetical subset of images, versus the image position (Z-coordinate). The blue line in the graph shows the slope of the red line, which reflects how the X-coordinate varies from one image to the next. The image for which the slope is zero (vertical), is the one (image 40 in this example) containing the most anterior point (minimum X-coordinate). If the computation in Step 204 above fails to contain a suitable point in the subset of images to correspond to the extreme in the mathematical formula, then a new subset of images can be analyzed. For example, and without limitation, the original subset could include the middle image 30 in a series along with four adjacent exemplary images 21, 23, 25, 27 and 32, 34, 36, 38 on either side (laterally in the Z-axis). If this subset had not found a suitable extreme point, then the new subset of images can include five images 30, 32, 34, 36, 38 from the original subset, along with four additional images 40, 42, 44, 46 adjacent on one side or the other, where image 38 would be the middle image. The choice of the new subset depends on the nature of the failure of the original subset.

If the original subset was rejected because the extreme point was found to lie outside the subset of analyzed images (none of the analyzed images had slope of zero), then the system seeks to shift the subset of images toward where the minimum would be—that is, in a direction of a downward slope of the mathematical function. So, the system computes the slope 244 of the quadratic formula at the center point of each image (e.g., blue line in FIG. 17). If the slope is positive (X-axis coordinate increases with increasing Z-axis coordinate; as with the blue line in the figure), then the new subset is chosen toward the lower Z-axis coordinates (as in the figure below; to where the X-axis coordinates are less). Conversely, if the slope is negative (X-axis coordinate decreases with increasing Z-axis coordinate), then the new subset is chosen toward the higher Z-axis coordinates.

Once a new subset is selected, it is analyzed in the same fashion as was the original subset, and the process recurses until an image with a suitable minimum X-axis coordinate for the top anterior skull portion as a reference feature for this example is found. This image is taken as a good initial guess for a mid-line image where the 3D position of the inferior portion of the basion may appear.

3.4 Check Coordinates in Images for Anatomical Feature Position in Step 208

The methods of steps 204 and 206 described above may be used to help identify the preferred images and subsets of images to search for anatomical features, or also for finding the particular anatomical features themselves. For example, finding the most anterior (across images) of the top skull point (within each image) helps identify images medial to the skull that most likely will also contain the basionand portions of the basion. The inferior portion of the basion within each image is found as the inferior portion of the anterior skull surface. But, in three dimensions across the various images the 3D position of the most inferior portion of the basion may be found by considering the vertical, Y-coordinates. Because of the curvature of the foramen magnum of the skull, and because the typically anterior, upward tilt of the skull, the 3D position of the inferior portion of the basion will have the highest vertical position (maximum Y-axis coordinate) among its neighbors across adjacent images. So, the mathematical methods described in steps 204 and 206 may be used to consider the Y-coordinates, and identify features, such as the inferior portion of basion, in three dimensions. In similar fashion, other anatomical features could have spatial relationships with surrounding structures, and be found with these methods. So, the system finds the 3D position of the inferior portion of the basion by looking for the maximum Y-axis coordinate for the inferior portion of the basion among the analyzed images. In an alternative embodiment, the system could start with the image assumed to be a good initial guess from Step 204 above, then look at the positions of inferior portion of the basion Y-axis coordinates from neighboring images, and if either is greater, then it increments to that image and continues searching until it finds the image of maximum Y-axis coordinate. This point can be taken as the 3D position of the inferior portion of the basion. As a further refinement, the 3D position can be established by interpolation between images.

As mentioned above, the mathematical function can include a quadratic function fit, although other mathematical functions can be applied. The function extreme computation that was applied to the skull top portion could instead have been applied directly to the basion position. Practice has suggested that the trajectory of the skull portion is more regular and predictable, and covers a broader range of images, than that of the basion position. So, for the sake of robustness, it seems to work well to start with the top skull portion, and then move to the basion position once a good midline image has been found for this particular anatomical feature.

3.5 Check Coordinates of Images for Second Anatomical Feature in Step 210

The process for finding the second anatomical feature is similar to that for finding the first anatomical feature. In the particular basion-dens example, the dens is generally aligned in or close to the same image as the basion due to the anatomical structures and orientations and so subsequently finding the dens is somewhat simpler than initially finding the basion. The process for finding the dens benefits from already having a subset of medially-located images identified from the search for the basion. The search uses the same subset of images for the basion to search for the dens. Naturally, this checking of coordinates and consequent search could vary with other preselected anatomical features.

The preselected portion of the dens within each image is taken to be the superior portion of the second cervical vertebra. The true 3D position of the superior portion of the dens is assumed to be the highest point (maximum Y-axis coordinate) on the second cervical vertebra (the axis) across the various images. Candidates for the 3D position of the superior portion of the dens are assumed to have already been located in each of the subset images by the earlier processing described above. The system looks across these images to find which image position of the superior portion of the dens is the highest (maximum Y-coordinate), and this point is taken as the true 3D position of the superior portion of the dens.

The steps to identify the positions of the preselected anatomical features can include computing a simple numerical derivative of the Y-axis coordinate as a function of the Z-axis coordinate. That is, the question in each step from one image to the next is how much does the Y-axis coordinate change. This change should approach zero near the peak.

3.6 Select Best Position of Anatomical Feature in Step 212

It has been found that occasionally the dens can reach a flattened plateau region with equal Y-axis coordinates across several successive images, and greater than those of neighboring images. In such a case, no clear maximum position will likely be found to establish the compiled 3D position of the superior portion of the dens. In such cases, the system can search the coordinates in the images having the plateau to determine the best position of the superior portion of the dens. Generally, the best position will be the center of the coordinates of the plateau of the superior portion of the dens among the images. Thus, if a clear maximum is not found among the image positions of the dens from the subset images in Step 210, the central coordinates of the plateau is taken as the compiled 3D dens position. As a practical matter of processing, if the number of plateau images is even, then image index can be just rounded down. While this example focuses on the dens due to its particular anatomical structure, this position adjustment can be applied to other preselected anatomical features.

4.0 Compute Distance Between Anatomical Features, Compare Normative Data and Report Results in Step 300

FIG. 18 is an exemplary flowchart expanding on and detailing the steps within FIG. 6 step 300 for computing the distance between the first and second preselected anatomical features, comparing to normative date, and reporting the results from the flowchart of FIG. 6. So far, the method and system have been focused on identifying the positions of the preselected anatomical features, such as the exemplary 3D position of the inferior portion of the basion and the 3D position of the superior portion of the dens. For the basion-dens example, this computation involves calculating the basion-dens interval (BDI), which has been shown to be representative of the risk for OCC injury. That is, if the BDI is greater than a certain value, then the likelihood of OCC injury is elevated, and the physician should investigate further.

4.1 Compute Distance Between Anatomical Features in Step 302

Calculation of the distance can be made, once the coordinates of the two positions are known. In some embodiments, the system finds the positions of the anatomical features by 3D coordinates in pixel space. Because the raw image data contains the pixel dimensions and the slice thickness between adjacent images, the pixel based coordinates or calculations can be scaled to true 3D coordinates or true dimensional calculations.

While much of the above description has referenced 3D coordinates and positions, it is understood that the positions can be processed and/or computed in 2D by ignoring the depth dimension in the Z-axis between images. Thus, the distance between the anatomical features can be computed in 2D, by ignoring the depth dimension between images, or in 3D, by including the distance between images. If both the 3D basion and 3D dens positions appear in the same image, then the 2D and 3D calculations will be identical.

Because manual evaluation of the CT images by a physician or technician may tend to focus on a single image, and just locate appropriate basion and dens positions within that one image, the calculation of the 2D BDI by the system may be of interest. However, one advantage of the automated system and method described herein is that it scans across multiple images and computes the true 3D distance. For example, a patient exhibiting substantial depth displacement between basion and dens may be at high risk of undetected OCC injury, or else may have had a poorly performed or aligned CT imaging. The automated method and system described herein can compensate and account for either occurrence 4.2 Compare Distance to Normative Data in Step 304

For some embodiments, just the calculation of the distance between the anatomical features may be sufficient. However, when appropriate, the system can compare the computed distance to normative data. The normative data may be obtained by third parties and reference sources and may be stored in data files in various electronic media capable of being at least read.

For the basion-dens example, the BDI can be compared with normative data of known conditions, such as BDI measurements from non-injured patients. The normative data may show a threshold. For example, Dr. Chaput's research, noted above, has developed normative data and determined a distance threshold based on CT images that can be used as a comparison value to assess risk of OCC injury. If a measured BDI exceeds this distance threshold, then an elevated risk is indicated.

4.3 Report Results in Step 306

The results can be reported in various degrees of details. The report can simply be a positive or negative indication of exceeding the threshold, if any, and may be useful for an attending physician to prompt for further investigation. Other reports could include the image or images selected that contain the preselected anatomical features and marking such features on the image or images in 2D and 3D, the distance as a numerical value and graphically indicated, a 3D modeled composite of the shape of one or both of the anatomical features, a comparison of the numerical value to the threshold value with a percentage of deviation, and other data as may be useful. While the report is not intended to be a diagnosis, the report is believed to be useful for medical personnel to consider and make further tests or examinations for a diagnosis as necessary.

5.0 Further Alternatives

There are enhancements to the above method and system that may be included, but are not required for operation. One such enhancement that is currently used in the method and system is a refinement to the position of the preselected anatomical feature within each image.

5.1 Refining Positions of Anatomical Features Using a Centroid Method

The basic approach of the method and system to locate the anatomical features, such as the basion and dens, depends on use of a pixel intensity threshold value to distinguish bone from non-bone, as described above. The procedure does a good job at locating the dens, currently estimated to be within about a millimeter of its true position. However, different portions of the bone tend to have different densities and therefore different pixel intensities, and so a single intensity threshold may provide room for improvement to more uniformly delineate bone and non-bone. A variation of determining bone and non-bone pixels is using the below described gradient method. The gradient method looks not at just the pixel intensities, but at how those intensities change. There is a steep change from lighter to darker pixels across lines where bone becomes non-bone. The gradient method takes advantage of that change to fine-tune the estimated position of the anatomical feature. It looks in the vicinity of the approximate position of the anatomical feature for the line of steepest intensity decline, and, for example, the highest Y-axis coordinate along that line, (or lowest Y-axis coordinate depending on the particular feature being searched).

The method works by first computing a gradient direction and magnitude for each pixel in the vicinity of the approximate feature position. The gradient may be determined using a centroid approach. That is, for each pixel an intensity centroid is evaluated for a window with a certain dimension, such as 8 pixels wide and 8 pixels high centered on the pixel. The size of this window can be varied, but should be fairly small and regional to the pixel. The intensity centroid represents the position, relative to the pixel position, where the pixel intensities are central. Pixels with higher intensities will draw the centroid their way, while pixels with lower intensities will not. The concept is similar to a mass centroid, which represents the center point of mass (or gravity), but with pixel intensities instead of mass. The formulas for computing the intensity centroid are:

$$\text{Centroid } X\text{-axis coordinate} = \text{sum of } [(\text{pixel } X\text{-axis coordinate})*(\text{pixel intensity})]/\text{sum of } [\text{pixel intensities}]$$

$$\text{Centroid } Y\text{-axis coordinate} = \text{sum of } [(\text{pixel } Y\text{-axis coordinate})*(\text{pixel intensity})]/\text{sum of } [\text{pixel intensities}]$$

The centroid position relative to the pixel position represents the distance and direction in which most of the intensity lies. So, the centroid position reflects both a gradient direction and magnitude. That is, the direction from the pixel to the centroid is a direction of increasing intensity, and the distance from the pixel to the centroid is a measure of gradient magnitude. The gradient direction and magnitude are computed for each pixel in the vicinity of the approximate feature position. The system can then search in the generally expected direction of the anatomical feature guided by the gradient direction and magnitude.

In the BDI example, once the gradient direction and magnitude are computed for each pixel in the vicinity of the approximate feature position, the system can search for the most vertically-upward direction, and the pixel with the highest gradient magnitude. That pixel is taken to be the refined 3D dens position. For the exemplary basion, the system would look for the most vertically-downward gradient.

5.2 Characterizing an Anatomical Reference

In some embodiments it may be advantageous to characterize an anatomical reference. In such embodiments, the data can be stored in a database and used as a comparative reference during searching techniques or other processes.

Figure 19:
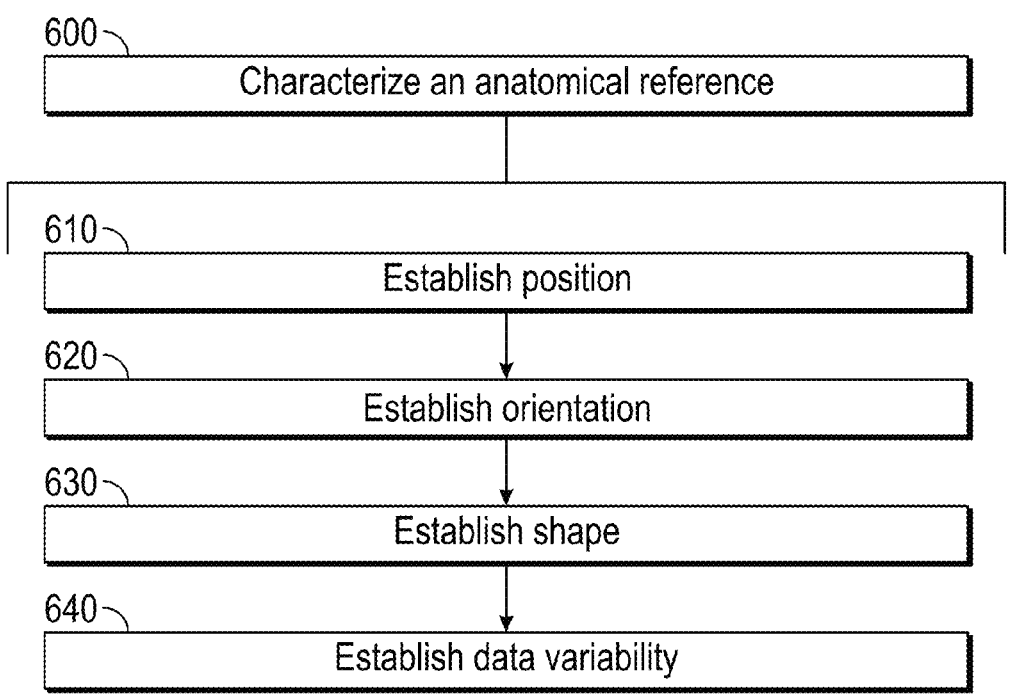
FIG. 19 is an exemplary flowchart expanding on the step 600 in FIG. 6 for characterizing an anatomical reference.

FIG. 19 is an exemplary flowchart expanding on the step 600 in FIG. 6 for characterizing an anatomical reference. In general, the characterization of an anatomical reference in Step 600 includes establishing a position of the reference in Step 610 on an image containing the anatomical reference. Establishing the orientation of the anatomical reference in Step 620 can provide a uniform starting point for a comparative analysis with other anatomical structures. Establishing the shape of the anatomical reference in Step 630 helps provide the data for comparison with shapes of the other anatomical structures. Because anatomical references may vary, multiple anatomical references can be characterized to establish a range of variability and any acceptance criteria for following under that range. Thus, one of the steps includes establishing the data variability of a plurality of anatomical references in Step 640.

Figure 20:
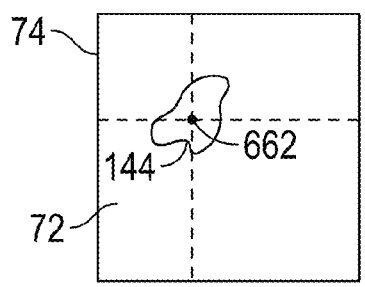
FIG. 20 is a schematic image that includes an exemplary anatomical reference to establish a position of the anatomical reference.

FIG. 20 is a schematic image that includes an exemplary anatomical reference to establish a position of the anatomical reference. In Step 610 of FIG. 19, an image 74 is examined to locate generally an anatomical region 72 and more specifically the anatomical reference 144. A centroid 662 of the anatomical reference 144 is determined by taking an average location of all the pixels in the cross-sectional image of the anatomical reference. For purposes of characterizing the anatomical structure, the structure should be reasonably well-defined around the edges. As discussed herein, there are various methods of defining location of the edges. Thus, the process of characterizing the anatomical reference could involve an additional step of determining an intensity threshold to establish the proper shape of the anatomical reference.

Figure 21A:
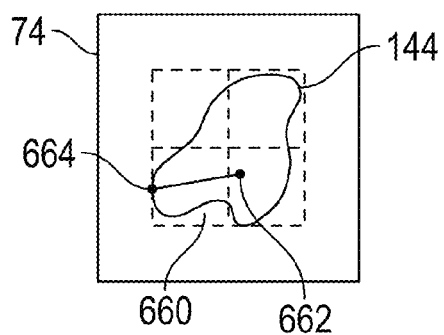
FIG. 21A is the schematic image of FIG. 20 with subdivisions to establish a point of interest on the anatomical reference.
Figure 21B:
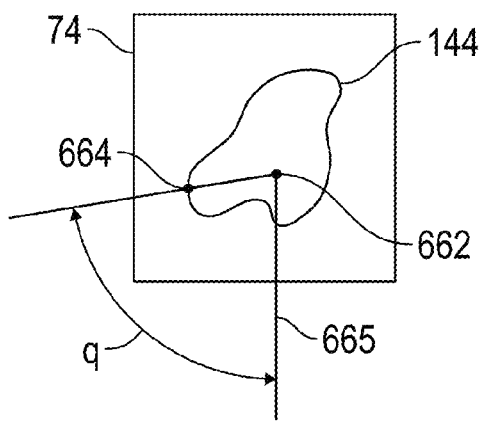
FIG. 21B is a schematic image of FIG. 21A with an angle to establish the orientation of the anatomical reference.

FIG. 21A is the schematic image of FIG. 20 with subdivisions to establish a point of interest on the anatomical reference. For Step 620 in FIG. 19, the orientation of the anatomical reference 144 can be determined. The image 74 can be divided into subdivisions generally starting from the centroid 662. For example, the image 74 can be divided into quadrants with the dividing lines intersecting the centroid 662, although other orthogonal or radial subdivisions of the image can be made. An arbitrary subdivision 660 can be chosen as a quadrant to start determining features in mapping the shape of the anatomical reference 144. In general, it is envisioned that a consistent starting subdivision will be chosen among anatomical references, so that comparative analysis can be easier made with a common starting point. While in the example shown in FIG. 21A, the lower left subdivision is chosen, it is understood that other subdivisions could be chosen. In the subdivision 660, a distance is determined from the centroid 662 to the farthest point 664 on the edge of the anatomical reference 144 in that subdivision 660. FIG. 21B is a schematic image of FIG. 21A with an angle to establish the orientation of the anatomical reference. Once the farthest point 664 is determined from the centroid 662, the angle θ is determined of the furthest point relative to some datum. For example, the datum can be the vertical axis 665, corresponding to a Y-axis in an orthogonal system. A horizontal axis (generally, an "X-axis"), or other reference datum could be used, with the intention that such datum be uniformly used across multiple anatomical references to assist in comparative analyses. Thus, the position of the centroid 662 and the angle θ of the furthest point in a chosen subdivision of the image 74 has been determined relative to datum axis.

For establishing the shape of the anatomical reference in Step 630 of FIG. 19, the point 664 that is used to determine the orientation of the anatomical reference 144 can also be used as a starting point for this determination. The term "shape" is used broadly to include digital data of the distance from the centroid 662 around the edge of the anatomical reference 144 in a given direction. The digital data can be mapped into a chart described below. While the "shape" is drawn in a visual form in the figures for illustrative and conceptual purposes, the actual digital data does not need expressing in a visual form.

Figure 22:
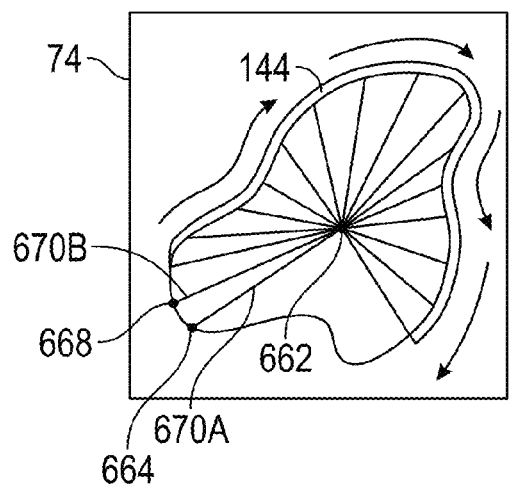
FIG. 22 is a schematic image of the anatomical reference showing a plurality of measurements around a periphery of the anatomical reference.

FIG. 22 is a schematic image of the anatomical reference showing a plurality of measurements around a periphery of the anatomical reference. The shape of the anatomical reference 144 in the image 74 can be digitally mapped by determining the distance from the centroid to the periphery 668 of the anatomical reference at multiple points around the parameter. For high resolution, each pixel around the periphery 668 can be measured from the centroid 662. In other embodiments, incremental numbers of pixels can be skipped between measurements, depending on the resolution desired. In the exemplary embodiment shown in FIG. 22, a series of distances at incremental steps around the periphery 668 from the centroid 662 are measured. For example, a measurement from the centroid 662 to the starting point 664 at the periphery 668 gives a distance 670A. An incremental number of pixels in a clockwise direction can give a distance 670B from the centroid 662 to the incremented pixel on the periphery 668. The process can continue around the periphery 668 until the anatomical reference is mapped back to the starting point 664. While the direction is described as clockwise, other directions or even other mapping techniques can be used with the general concept that it is advantageous that a consistent mapping procedure will be used that can be applied across multiple anatomical references and structures for comparative analyses.

Figure 23A:
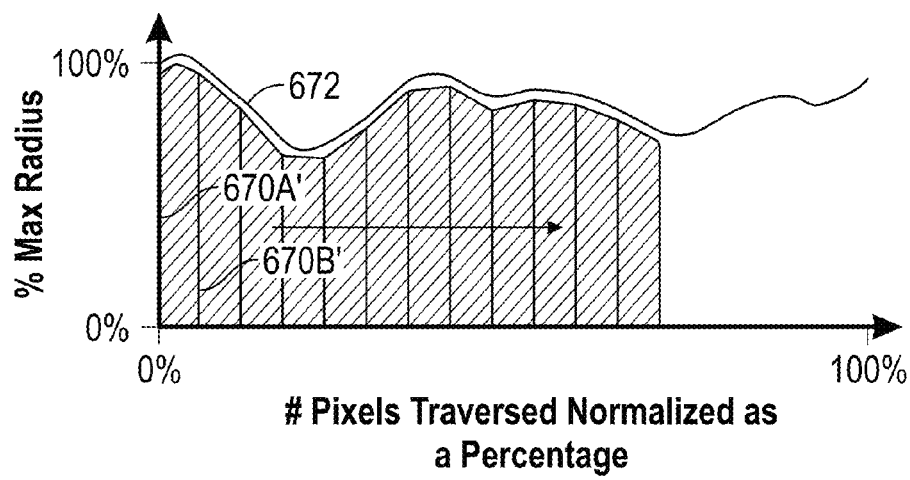
FIG. 23A is a chart illustrating an exemplary mapped shape of the periphery of the anatomical reference.
Figure 23B:
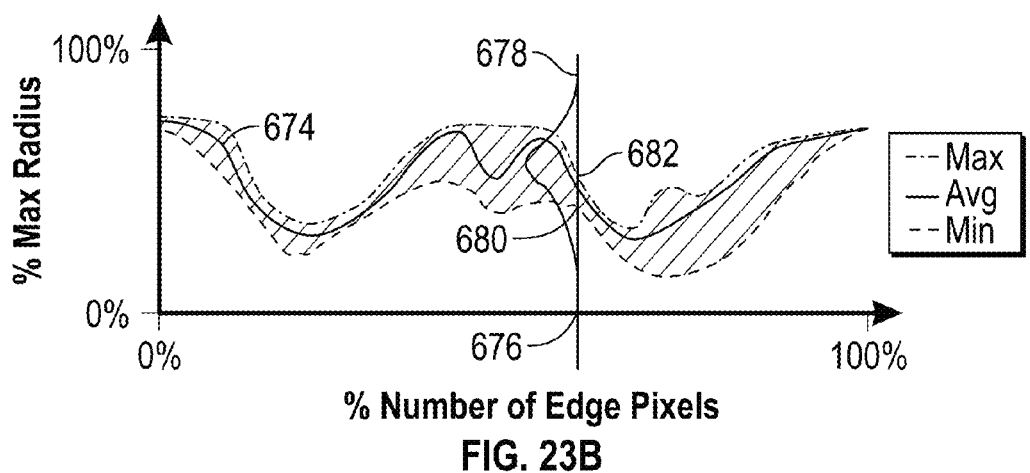
FIG. 23B is a chart illustrating exemplary mapped shapes of the peripheries of a plurality of anatomical references with data variability from the anatomical references.

FIG. 23A is a chart illustrating an exemplary mapped shape of the periphery of the anatomical reference. FIG. 23B is a chart illustrating exemplary mapped shapes of the peripheries of a plurality of anatomical references with data variability from the anatomical references. The figures will be described in conjunction with each other. The chart shows a linear arrangement of the distances 670A, 670B, and so forth around the periphery 668 of the anatomical reference 144. The horizontal X-axis in the chart represents the number of transversed pixels in establishing the shape that have been normalized as a percentage of the periphery. The vertical Y-axis is the length of the distance from the centroid to the particular pixel at the periphery 668 that have been normalized as a percentage of the longest distance between the centroid and the periphery. The first point shows the distance 670A' that represents a normalized percentage of the distance 670A measured and shown in FIG. 22 of the distance between the centroid 662 and the starting point 664. The following line shown in the chart is distance 670B' that represents a normalized percentage of the distance 670B measured and shown in FIG. 22. The process is continued until the distances around the periphery 668 are graphed and shown in the chart.

A best fit line can be interpolated between the normalized lengths 670A', 670B', and so forth to establish a mapped shape 672 of the anatomical reference. This mapped shape 672 characterizes the anatomical reference peripheral shape in a linear fashion and represents the underlying digital data. The mapped shape 672 can be used to compare different shapes of other anatomical structures to determine if there is a correlation of the shape of the anatomical structure to the mapped shape of the anatomical reference. If there is a correlation in the shapes, then likely the anatomical structure would be identified as a specimen of the anatomical reference that was mapped.

Because the particular anatomical reference may vary in size from image to image, person to person, in orientation, or some other variation of shape, a further mapping of other anatomical references can be used to aggregate data for the particular anatomical references. As shown in FIG. 23B, the anatomical reference data from multiple mapped shapes of same anatomical references can create an average anatomically mapped shape 674 with a distribution of data 678 at any particular point 676. One or more tolerances can be designed into the data, so that a lower tolerance 680 and an upper tolerance 682 can establish a spread of data for a given point around the periphery 668 described above. The tolerances can be established on an desirable basis, such as a percentage, statistical distribution of sigmas, or other criteria as may be appropriate for the particular measurements. A comparative analysis of a correlation (which can be predetermined by the user) between a shape of an unknown anatomical structure to a known anatomical reference could determine whether the anatomical structure is a specimen for the anatomical reference. In general, if a shape in question of an anatomical structure exceeds the tolerance, such as a certain number of times, the anatomical structure can be rejected as not having a sufficient correlation to the shape of the anatomical reference that has been mapped. The number of deviations that exceed the tolerance can be determined by the accuracy of the data, the number of samples measured, or other criteria. For example and without limitation, the upper and lower tolerances can be determined by using extreme specimens and then expanding the data by 10% (or other percentages) so as to accomplish a wider band of potential shapes of anatomical structures that could correlate with a mapped anatomical reference.

Figure 24A:
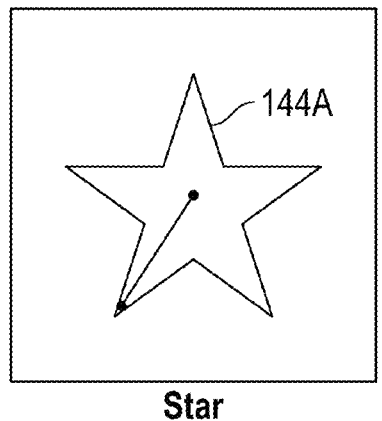
FIG. 24A is a schematic image of an exemplary shape of a reference.
Figure 24B:
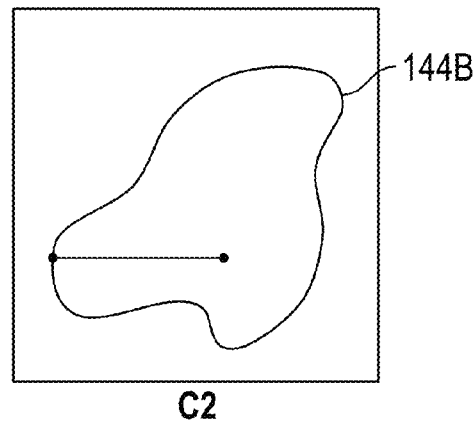
FIG. 24B is a schematic image of another exemplary reference.
Figure 25:
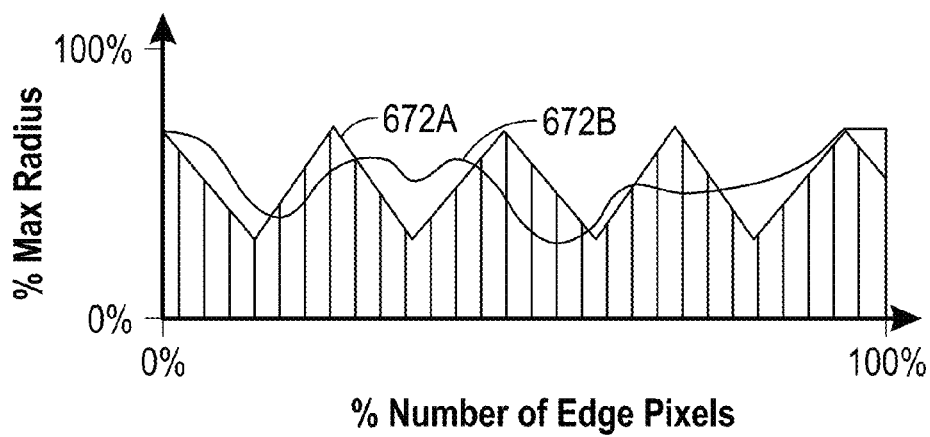
FIG. 25 is a chart contrasting the mapped shapes of the two exemplary references in FIG. 24A and FIG. 24B.

FIG. 24A is a schematic image of an exemplary shape of a reference. FIG. 24B is a schematic image of another exemplary reference. FIG. 25 is a chart contrasting the mapped shapes of the two exemplary references in FIG. 24A and FIG. 24B. The figures will be described in conjunction with each other. In FIG. 24A, an anatomical reference 144A can be mapped in the manner described above and as shown in FIG. 25 to produce a shape 672A. Similarly, the anatomical reference 144B as shown in FIG. 24B can be mapped to produce the shape 672B, also shown in FIG. 25. Thus, each anatomical shape can have its unique signature curve for comparative analysis to other anatomical structures and any resulting correlation.

5.3 Determining a Pixel Intensity Threshold

Figure 26:
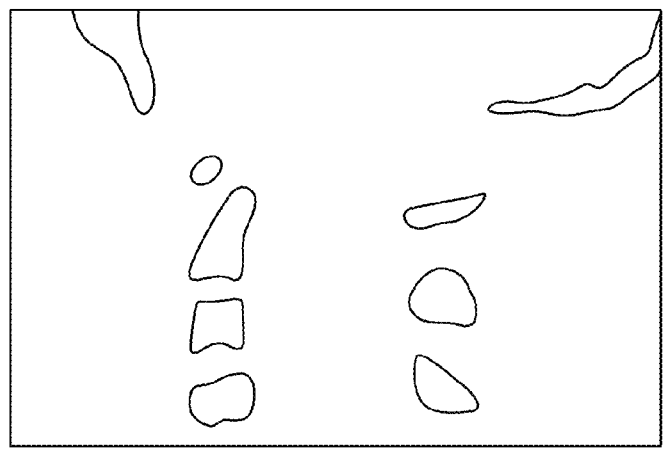
FIG. 26 is an exemplary image having anatomical structures.

FIG. 26 is an exemplary image having anatomical structures. In many imaging processes, bones and other anatomical references represent the brightest aspects in the image. However, not all anatomical structures in the image appear as bright as each other, nor is an edge of the anatomical structure consistently bright along the same anatomical reference relative to other edge portions or the central portions of the anatomical structure. In processing the images digitally, it is advantageous to understand which pixels represent anatomical structures compared to which pixels represent soft tissue, or even an absence of either. Intensity thresholding and processing of pixels has been described above to determine the need for an intensity threshold value to enable digitally processing of the images. An aggressive thresholding method that requires a brighter intensity may "dissolve" some of the anatomical structures such as bones in a given image, because their intensity level did not meet the threshold requirements. On the other hand, a timid approach may make the edges of anatomical structures larger than they really are or even combine adjacent anatomical structures into one structure due to an overinclusive number of pixels that apply to a lower threshold.

The goal is to have an adequate threshold that neither is overly aggressive or underly timid to enable an accurate digital image of the anatomical structure for further processing. While thresholding has been described above, the below description includes an alternative thresholding process that may be more robust in processing and potentially more accurate.

Figure 27:
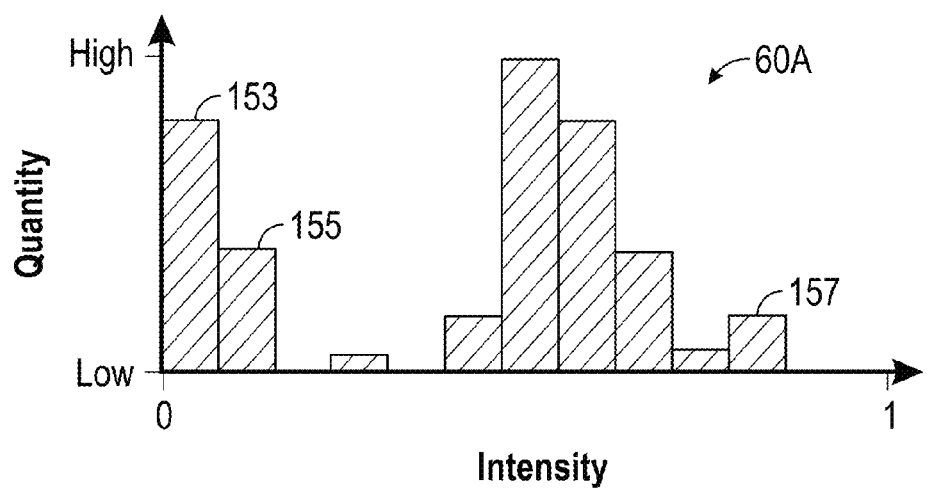
FIG. 27 is an exemplary chart of a histogram of pixel analysis for establishing a pixel intensity threshold.

FIG. 27 is an exemplary chart of a histogram of pixel analysis for establishing a pixel intensity threshold. To determine the initial threshold, an image can be scanned and a histogram developed. FIG. 27 shows an exemplary histogram 60A, as a variation to the histogram described in FIG. 8. The number of pixels and different intensities can be divided into bins, and the number of pixels having an intensity value fitting between the ranges of each bin can be charted to develop the histogram. For example, the bin 153 can have a certain number of low intensity pixels (including zero intensity indicating no structure), bin 155 can have a smaller amount of pixels that have a somewhat increasing level of intensity, and so forth until the maximum pixel intensity is shown in bin 157 having a certain amount of pixels therein.

Figure 28:
FIG. 28 is an exemplary chart of a probability density function based on the histogram of FIG. 27.

FIG. 28 is an exemplary chart of a probability density function based on the histogram of FIG. 27. A probability density function can be generated using the histogram in FIG. 27 by calculating the quantity of pixels in each particular bin divided by the total number of pixels to develop the probability that some pixel will be in a given range of intensities level for the image. The sum of the probabilities will be a unitary value of 1. Thus, the value of the probability 154 on the Y-axis of the pixels in bin 153 shown in FIG. 27 is shown as a relatively high number due to the relatively high number of pixels in the bin 153. The value of the probability 156 in FIG. 28 is shown as the probability of the pixels 155 in FIG. 27.

Figure 29A:
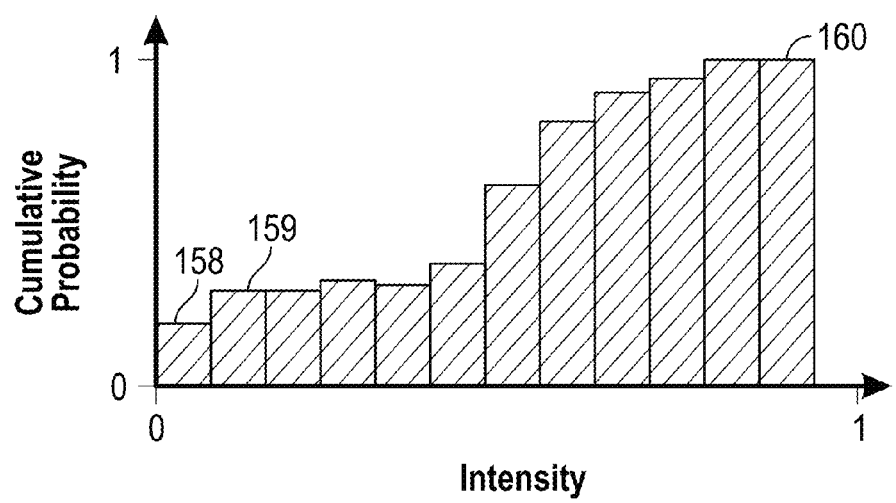
FIG. 29A is an exemplary chart of a cumulative density function based on the probability density function of FIG. 28.

FIG. 29A is an exemplary chart of a cumulative density function based on the probability density function of FIG. 28. A cumulative density function can be generated using the probability density function. The cumulative density function sums the probabilities of all the intensities from the starting intensity in order through the highest intensity. For example, the value of the cumulative density 158 in FIG. 29A is generally equal to the value of the probability 154 in FIG. 28, because the probability 29A is the first value. However, the cumulative density 159 in FIG. 29A is the sum of the probabilities 154 and 156. Likewise, the incremental cumulative densities are calculated on FIG. 29A until all the cumulative densities are calculated. The last cumulative density 160 will be the unitary value of 1.

Figure 29B:
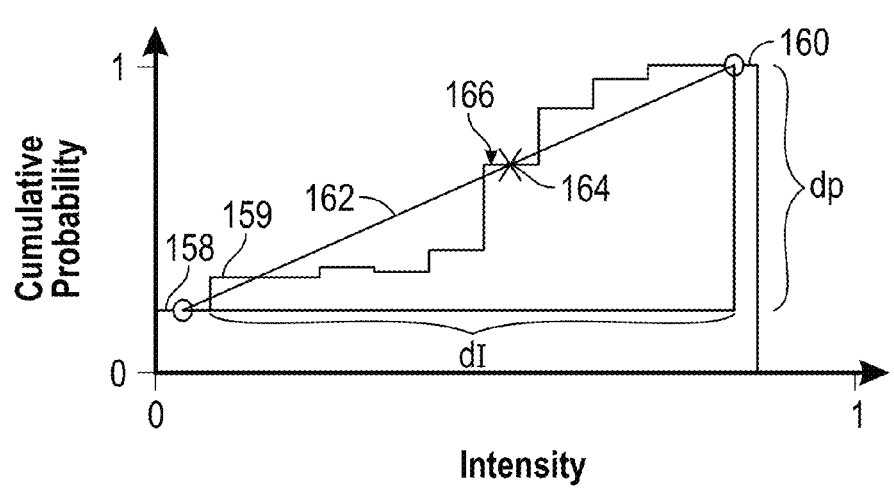
FIG. 29B is the cumulative density function chart of FIG. 29A with an exemplary line drawn between ranges on the chart and a point of intersection shown to assist in establishing a threshold level of intensity for the pixels.

FIG. 29B is the cumulative density function chart of FIG. 29A with an exemplary line drawn between ranges on the chart and a point of intersection shown to assist in establishing a threshold level of intensity for the pixels. The target image of the anatomical reference essentially has two intensity clusters: one is bone that is the brightest of the anatomical structure, and the other is nonbone generally that is dark and not including bony structure. The intensity clusters in the target image with the bright and dark images creates a sigmoidal distribution that is seen in the exemplary cumulative density function. An advantageous intensity threshold for separating the bright from the dark is where a sigmoid intercepts the cumulative intensity function. To find a threshold for the pixels that were measured in intensity, the slope of the cumulative density function can be determined. While the calculations are done digitally, for illustrative purposes, FIG. 29B shows the procedure. From a midpoint of the cumulative density 158 to the midpoint of the cumulative density 160, a line 162 can be drawn. The line 162 can be interpreted as the cumulative density function of an imaginary image that has the same range of pixel intensities as the measured image but has a uniform distribution of intensities in the bins. Starting from the highest intensity of the cumulative density at 160 and following along the line 162, the first point of intersection 164 of the line 162 with the cumulative densities is at the cumulative density 166. While the line 162 is shown as a straight line, it is to be understood that different geometrical shaped lines can be drawn digitally, including parabolic, elliptical, and other shapes as may be appropriate for the particular threshold, anatomical reference, or other considerations. The intensity of this thresholding technique can be adjusted by artificially changing the slope of the line, or the shape of the line.

5.4. Refining the Digital Shape of an Anatomical Structure in an Anatomical Region Despite being able to find a good threshold without using manual trial and error, the thresholding technique that inspects every pixel in an image will still be too conservative. The method involves recursive thresholding by repeating a threshold-finding process using subdivisions in an image near anatomical structures that are found in a previous pass of processing.

As described above, having too high an intensity threshold and too low of an intensity threshold can affect the resolution and shape of the anatomical references that are being sought. Thus, errors can be generated by having an inappropriate thresholding. The following technique describes how the shape of an anatomical reference can be determined to produce a more accurate shape.

FIG. 30A is a schematic partial image of an exemplary anatomical region. FIG. 30A includes an image 74 having two anatomical structures for purposes of illustration. A first anatomical structure 168 includes an edge 170 and an inside portion 172. A second and smaller anatomical structure 174 likewise includes an edge 176 and an inside portion 178. Generally, an image such as has been described above, will have a dark (such as black) region around the structures, a light (such as white) region for the edge, such as the edges 170, 176 of anatomical structures and a mid-level intensity level (such as grey) for the inside of the bony structures, such as the inside portions 172, 178, due to a lower density of bone than the edge of bone. Each different color can be considered a different attribute that is assigned to a given pixel.

FIG. 30B is a schematic exemplary first digital image of the image of FIG. 30A after a first processing pass using a predetermined intensity threshold. The image 74 can be processed with a first pass for intensity thresholding using one or more of the techniques described above to produce a resulting anatomical structure 180. Because the first pass results in a thresholding that is set too low in this example and because of the proximity of the first and second anatomical structures 168, 174, the resulting processed image results in the single anatomical structure 180 having a general peripheral shape that is the result of the combined shapes of the first and second anatomical structures and no dark or grey regions inside the structure 180. The regions outside the structure 180 are dark (black) in this example.

FIG. 30C is a schematic subdivided digital image of the image of FIG. 30A. Starting again with the image 74 of FIG. 30A, the image can be divided into at least two subdivisions 181, 182, and as a practical application into at least quadrants, although other numerical quantities of subdivisions can be used. Each subdivision can be separately processed using the threshold determination described in reference to FIGS. 27-29B to establish intensity thresholds per subdivision (or other intensity threshold techniques). Using the subdivisions and intensity thresholds for each subdivision yields a finer resolution than shown in FIG. 30B. In determining which subdivisions to process in a given image, a first determination is made as to whether or not the subdivision contains an anatomical structure. If the subdivision contains at least a portion of an anatomical structure, the subdivision is processed to determine a new intensity threshold for that subdivision. If the subdivision does not contain at least a portion of an anatomical structure, then the subdivision is not processed. To determine whether or not the subdivision obtains a threshold or an anatomical structure, the last threshold intensity is used.

FIG. 30D is a schematic exemplary second digital image of the image of FIG. 30C after a second processing pass with the intensity threshold determined per selected subdivision. In this example, all four subdivisions of FIG. 30C contained at least a portion of the anatomical structures 168, 174 and were processed per subdivision to produce the results in FIG. 30D. With the processing by subdivisions, a finer resolution of the outer shape of the anatomical structures 168, 174 is generated, so that both anatomical structures are apparent rather than the combined structure 180 shown in FIG. 30B. Further, the thresholding has been refined by using the smaller subdivisions such that the lighter density inside portions of the anatomical structures now appear as a different color (attribute) than the inside portions of the structure 180, shown in FIG. 30B.

FIG. 30E is a schematic further subdivided digital image of the image of FIG. 30D. The image 74 in FIG. 30D can be further subdivided into smaller subdivisions, such as subdivisions 183, 184, 185, 186, as shown in FIG. 30E. For example and without limitation, the quadrants shown in FIG. 30D can each be divided into their own quadrants. Each of the smaller subdivisions can be examined as to whether a portion of an anatomical structure exists in the smaller subdivisions. If a smaller subdivision includes a portion of an anatomical structure, then the subdivision can be processed for an intensity threshold for that particular smaller subdivision.

FIG. 30F is a schematic exemplary a further digitally processed image of the image of FIG. 30E after a third processing pass with the intensity threshold determined per selected subdivision. The smaller subdivisions 183, 184, 185, shown in FIG. 30E, did not have at least a portion of an anatomical structure and therefore were not processed in generating the image of FIG. 30F. However, a piece of the anatomical structure 168 extends into the subdivision 186. Therefore, subdivision 186 is processed for an intensity threshold and the shape of the anatomical structure in the subdivision is further refined with the new intensity threshold. The rest of the subdivisions in the image 74 are screened for portions of anatomical structures and if present, then the subdivision is processed in like manner. This third pass with finer resolution can be used to modify the shape of the first and second anatomical structures 168, 174.

FIG. 31A is a schematic digital image showing the results of the processing of the image of FIG. 30F with one more pass for a fourth pass in like manner as described above. The difference in shapes of the anatomical structures between the third pass shown in FIG. 30F and the fourth pass shown in FIG. 31A is minimal, and the processing of the shapes can be finished. The number of passes can depend upon the change in shape of the anatomical structure(s) from the previous pass. If there is a minimal change in the shape between the previous pass and the current pass, then it can be presumed that the resolution of the shape has reached a sufficiently accurate image. For example, the accuracy could be a change in the anatomical shape of less than 10%, realizing that other parameters can be established. As a practical matter, it has been experimentally determined that about four passes generally result in a sufficiently accurate shape of the anatomical structure.

The processing can produce an image 74 where the inside portions of the anatomical structures are artificially dark indicating no anatomical structure in the inside portions, which can be factually inaccurate. For example, FIG. 31 shows the first anatomical structure 168 having a dark inside portion 172 indicating no anatomical structure exists in the inside portion, similar to the dark portion of the image outside the structure 168, when in fact the anatomical structure could be solid throughout the shape. Likewise, the anatomical structure 174 shows a dark inside portion 178, similar to the dark portion of the image outside the structure 174. This anomaly may occur for the anatomical structures 168, 174, because of the lower density of the inside portions 172, 178 compared to the higher density of the edge portions 170, 176 and the thresholding process.

The following steps may be used to refine the inside portions of the anatomical structures to reflect the reality of the structure. Additional processing of the image can change the attributes inside the anatomical structures to be consistent with the edge attributes of the anatomical structures. For illustrative purposes, the use of colors will be referenced below as an attribute that is changed for the images (whether digital or otherwise) with the understanding that other attributes can be used such as letters, numbers, marks, values, or other attributes associated with given pixels to differentiate portions of the images outside the anatomical structures, the edges of the anatomical structures, and the inside portions of the anatomical structures.

FIG. 31B is a schematic digital image of the image of FIG. 31A with a change in attributes. Black pixels (a first attribute) outside the anatomical structures and black pixels inside the anatomical structures can be changed to a dark grey (a second attribute) in FIG. 31B.

FIG. 32A is the schematic image of FIG. 30B without the subdivisions. FIG. 32B is a schematic image of edge pixels of the anatomical region shown in FIG. 32A. The figures will be described in conjunction with each other. The results of the first pass shown in FIG. 32A (and FIG. 30B) were to establish an overall intensity threshold determination of the image 74 as a whole. The overall threshold determination resulted in a larger periphery of the first and second anatomical structures 168, 174, so that the resulting anatomical structure 180 was actually a single structure larger in size than the actual structures. The image in FIG. 32A can be digitally processed to identify pixels of an edge of the anatomical structure 180, so that just an edge 186 of the anatomical structure 180 is shown in FIG. 32B. The edge 186 can be changed to a light grey (third attribute) that is a different attribute than the black (first attribute) and the dark grey (second attribute).

FIG. 33A is a schematic image of the edge pixels of FIG. 32B mapped with the anatomical reference shown in FIG. 31B. The edge 186 in FIG. 32B can be overlaid onto the anatomical structures shown in FIG. 31B to result in FIG. 33A. The overlay can be used to identify those pixels outside the anatomical structures from those pixels inside the anatomical structures even with the same attributes. The pixels identified as being outside the edge 186 can be changed from dark gray (second attribute) to black (first attribute).

FIG. 33B is a schematic image of FIG. 33A replacing pixels of an attribute with another attribute. Further, any dark grey region inside the edge 186, but outside the edges 170, 176 of the anatomical structures 168, 174 with their own color (in this example white as a fourth attribute) can be changed to black (first attribute). Thus, the inside portions 172 and 176 of the second anatomical structures 168, 174 respectively are protected from an attribute change while the external regions of pixels around the first and second anatomical structures in contact with the edge 186 are changed to a different attribute.

Figure 33C:
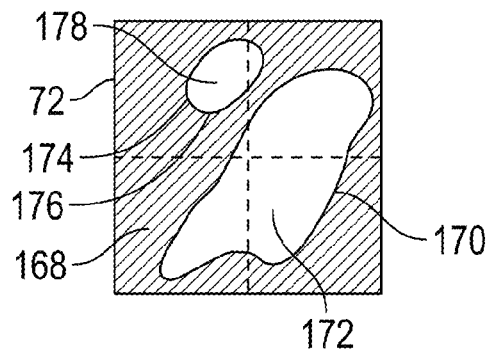
FIG. 33C is a schematic image of FIG. 33B replacing pixels of an attribute with another attribute to fill in solid structures of the anatomical region.

FIG. 33C is a schematic image of FIG. 33B replacing pixels of an attribute with another attribute to fill in solid structures of the anatomical region. Once the surrounding pixels outside the anatomical structures 1168, 174 are changed to different attributes, then the image can be further processed to change all remaining pixels of the dark grey (second attribute) of the inside portions 172, 178 to a selected color (attribute) that is generally different than the color (attribute) of the pixels outside the anatomical structures. In this example, the inside portions 172, 178 of the anatomical structures can be changed from dark grey (second attribute) to white (fourth attribute). The change will make the inside portion 172 consistent with the edge 170 on the first anatomical structure 168 Similarly, the change will make the inside portion 178 consistent with the edge portion 176.

Thus, the edge and the shape of the anatomical structures can be accurately depicted for further analysis.

5.5 Searching for Previously Characterized Anatomical References

The following steps describe an automated searching sequence based upon a previous characterization of an anatomical reference described in reference to FIGS. 20-25 and if appropriate, an intensity threshold established for anatomical structures found in the search in order to compare the anatomical structure with the intended anatomical reference.

Figure 34:
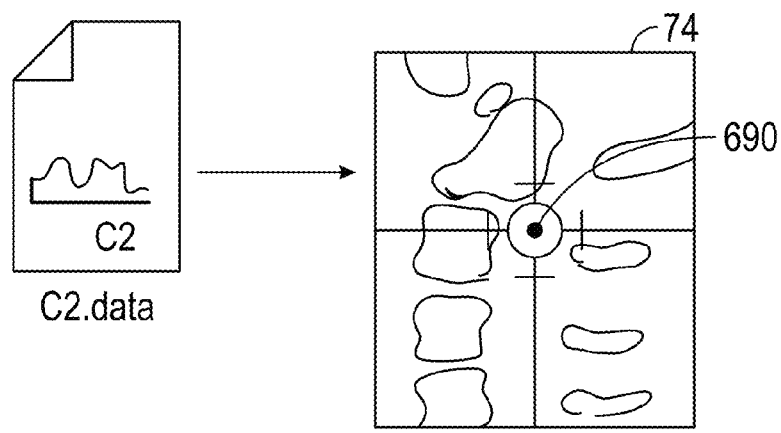
FIG. 34 is a schematic image of an anatomical region showing a starting point for a search for a previously characterized anatomical reference.

FIG. 34 is a schematic image of an anatomical region showing a starting point for a search for a previously characterized anatomical reference. An image 74 with multiple anatomical structures can be used to search for an anatomical reference among the anatomical structures and ultimately the anatomical feature that is desired. A starting point 690 can be used as a location to begin the search. The search can progress automatically for example by using an outwardly spiraling search. The search can continue and as anatomical structures are identified, the anatomical structure can be compared to the mapped shape of the desired anatomical reference. If there is a sufficient correlation, then the search can stop, because the anatomical reference has been found for the particular image being searched. If there is an insufficient correlation to the anatomical structure, then the search can continue in an outwardly expanding spiral until other anatomical structures are found, analyzed, compared, and either identified as the anatomical reference or continue the search for other anatomical structures. If an anatomical reference is not found within a predetermined search criteria, then the search can stop and either a new image analyzed or a different starting place for the same image used to start the search again. Optionally, during the search and identification of anatomical structures, intensity thresholds can be calculated, or recalculated as the case may be, to determine, or refine, the shape of the anatomical structure to facilitate the comparison with the shape of the anatomical reference.

Figure 35A:
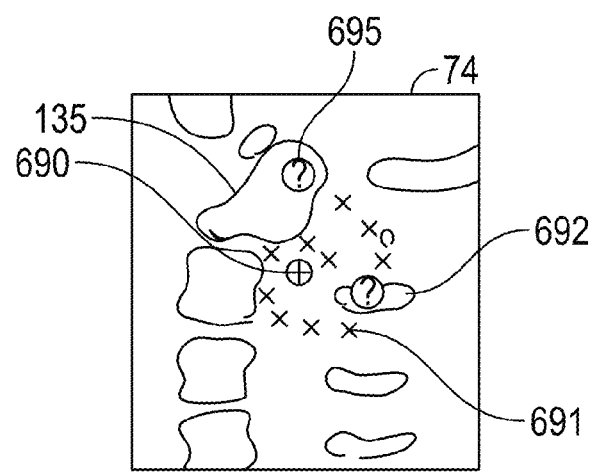
FIG. 35A is a schematic image of the image of FIG. 34 showing an exemplary search pattern encountering anatomical structures in the region for comparing with the previously characterized anatomical reference.
Figure 35B:
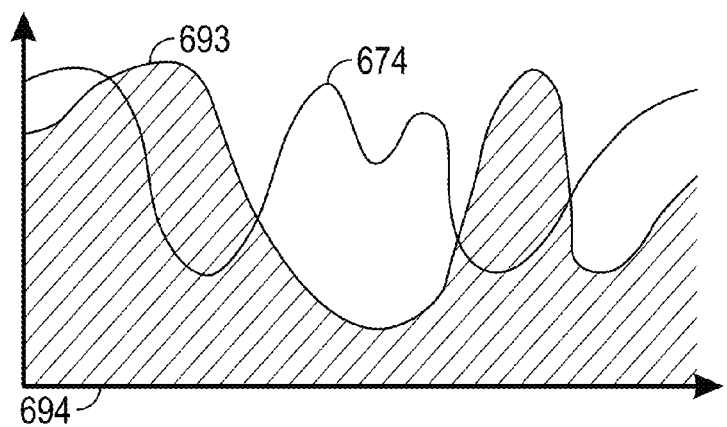
FIG. 35B is a chart comparing a mapped shape of a first structure in the schematic image of FIG. 35A with the mapped shape of the previously characterized anatomical reference.
Figure 35C:
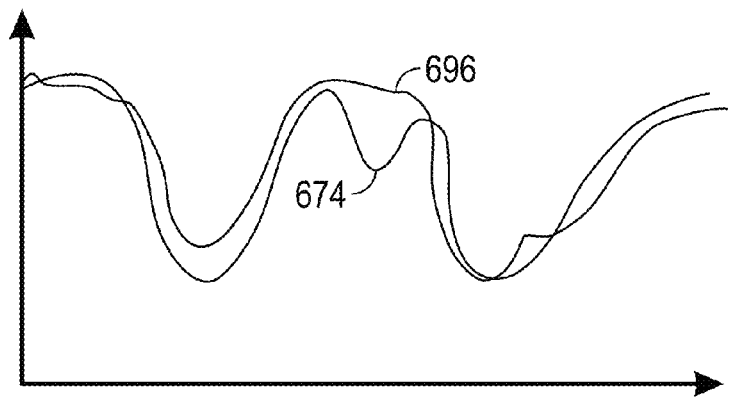
FIG. 35C is a chart comparing a mapped shape of a second structure in the schematic image of FIG. 35A with the mapped shape of the previously characterized anatomical reference.

FIG. 35A is a schematic image of the image of FIG. 34 showing an exemplary search pattern encountering anatomical structures in the region for comparing with the previously characterized anatomical reference. FIG. 35B is a chart comparing a mapped shape of a first anatomical structure in the schematic image of FIG. 35A with the mapped shape of the previously characterized anatomical reference. FIG. 35C is a chart comparing a mapped shape of a second structure in the schematic image of FIG. 35A with the mapped shape of the previously characterized anatomical reference. The figures will be described in conjunction with each other. A starting point 690 can be used to start the search routine using a pattern illustrated as X's on the FIG. 35A to create a pattern 691. In the illustrated embodiment, the pattern can be an outwardly spiral pattern in a counterclockwise direction, with the understanding that any search routine that progresses through the pixels of the image 74 can be used, and thus the spiral pattern is only exemplary. The pattern can search until it encounters an anatomical structure 692. The process can analyze the structure, establish the shape of the structure and a map of the structure such as described above in reference to FIGS. 20-23A. If appropriate, the shape of the anatomical structure 692 can be defined and/or refined, for example, by using the thresholding techniques described in reference to FIGS. 30A-33C. The shape of the anatomical structure 692 can be compared to the previous characterization of the desired anatomical reference.

FIG. 35B illustrates the mapped shape 693 of the anatomical reference 692 in comparison to the mapped shape 674 of the desired anatomical reference such as the second vertebrae 24 described in reference to FIG. 4, or more generally, the anatomical reference 135 described in other figures above. In FIG. 35B, the mapped shape 693 does not sufficiently correlate to the mapped shape 674 of the desired anatomical reference 135. For example, the shape 693 in question exceeds the tolerance of the shape 674 a certain number of times and is therefore rejected.

Returning to FIG. 35A, the search pattern 691 can continue until it finds another anatomical structure 695. The anatomical structure 695 can be mapped into a digital shape as described above and shown in FIG. 35C. Once the shape is determined, and any further intensity threshold adjustments made as described, then the shape 696 of the structure 695 can be compared to the previously mapped shape 674 of the desired anatomical reference 135. If there are a sufficient correlation of data, for example, such that the shape in question does not exceed the tolerance a certain number of times, then the anatomical structure 695 is identified as the desired anatomical reference 135. Once the desired anatomical reference is found such as, anatomical reference 135, the earlier described processing of finding the anatomical feature and its relative location to other anatomical features, as described above, can be performed.

Figure 36:
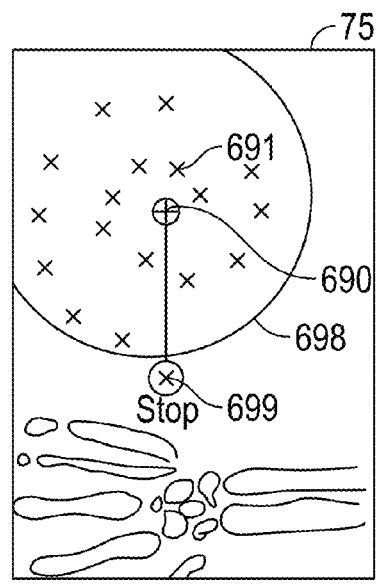
FIG. 36 is a schematic image of an anatomical region in which the search ends after not finding the previously characterized anatomical reference.

FIG. 36 is a schematic image of an anatomical region in which the search ends after not finding the previously characterized anatomical reference. FIG. 36 illustrates an image 75 in which the starting point 690 is established and the pattern of searching 691 is activated. The search continues until it exceeds predetermined search criteria. The search boundary 698 of the criteria is established, which may be a maximum radius from the starting point 690. Once the pattern exceeds the outer search boundary 698, such as at point 699, the search can stop.

Other search criteria can have different stopping points and the above maximum radius is only exemplary for the exemplary spirally expanding search pattern. Because the image 75 does not have any anatomical structure within the boundaries of the search routine or at least anatomical structure that correlates to an anatomical reference, a different starting point can be determined for the image 75, or the image can be disregarded as not being an image that would contain the desired anatomical reference.

Thus far, a number of steps have been described for automatically determining a BDI or other anatomical intervals using raw image data from a CT scan or other radiologic image. Following now is a description of one exemplary computing system that may be used to carry out these steps.

Figure 37:
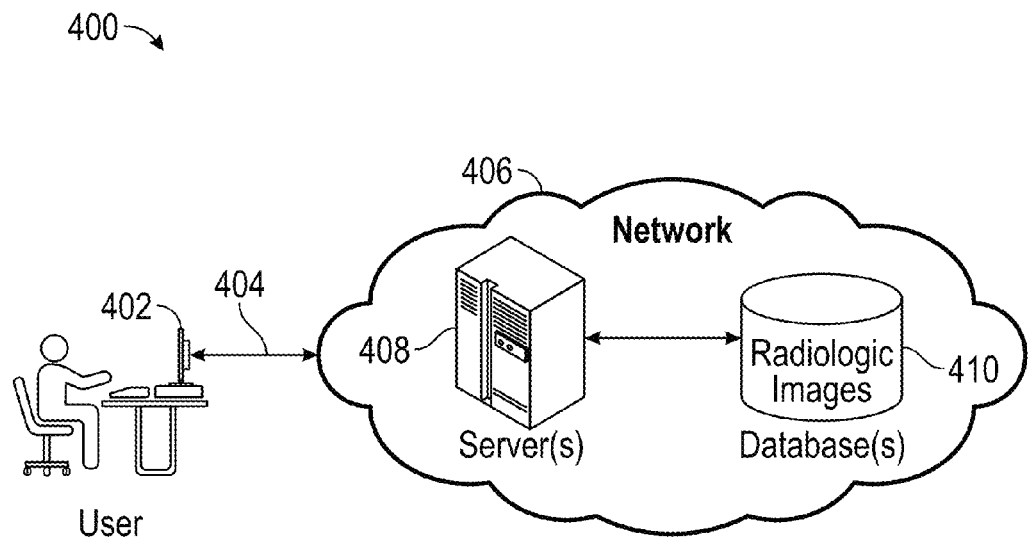
FIG. 37 illustrates an example of a computing system 400 in which the steps for automatically determining an anatomical interval, such as the BDI, may be implemented according to the disclosed embodiments.

FIG. 37 illustrates an example of a computing system 400 in which the steps for automatically determining an anatomical interval, such as the BDI, may be implemented according to the disclosed embodiments. As can be seen, the system can include at least one user computing device 402 connected via a network connection 404 to a network 406. In the present example, the user computing device 402 may be a desktop computer, notebook computer, and other similar user computing devices, and the network connection 404 may be a wired and/or wireless network connection. Alternatively, the computing device 402 may be a stand-alone system that does not interface with a network or network servers. One or more network servers 408 may be connected to the network 406 along with at least one database 410, which may be either an internal database that resides within the network servers 408, or a database that resides in a physically separate location from the network servers 408 (as shown here), depending on the constraints (e.g., size, speed, etc.) of the particular implementation. Note that the term "server" is used herein to include conventional servers as well as high-end computers, workstations, mainframes, supercomputers, and the like. Similarly, the at least one database 410 may be a relational database, operational database, or other suitable database capable of storing data and information, including radiologic images (e.g., CT scans, MRI, and so forth) used in the method of automatically determining a BDI disclosed herein or other anatomical features or measurements. For other embodiments, the images could be more generally anatomical images suitable for digital processing.

In general operation, the system 400 allows a user, such as a physician or other medical personnel, to select a set of anatomical images (such as radiological images) for a particular patient, identify a first anatomical region of interest in one of the images, initiate a BDI analysis of the images on the system, and thereafter review the results of the BDI analysis through the computing device 402. In other embodiments, the system 400 can more automatically select the anatomical region of interest and process the images without intervention by the medical personnel to produce the results that may alert the medical personnel to a condition that otherwise might be unsuspected and unknown. Within the system 400, the one or more network servers 408 access the anatomical images from the at least one database 410, processes and analyzes the images, compiles the results from the images to identify the location of the basion and the dens, and thereafter computes the BDI, compares the computed BDI with normative data, and outputs the results.

Figure 38:
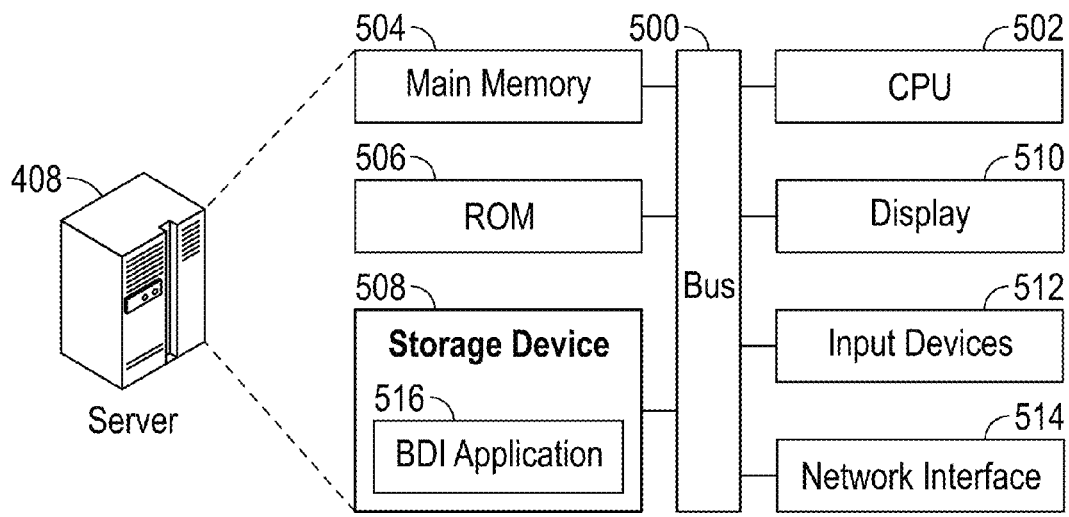
FIG. 38 illustrates an exemplary server that may be used as one of the one or more servers 408 on the computing network 406.

FIG. 38 illustrates an exemplary server that may be used as one of the one or more servers 408 on the computing network 406. As mentioned earlier, this server 408 may be any suitable computing system known to those having ordinary skill in the art, including a high-end server, workstation, mainframe, supercomputer, and the like. Such a server 408 typically includes a bus 500 or other communication mechanism for transferring information within the server 408 and a CPU 502 coupled with the bus 500 for processing the information. The server 408 may also include a main memory 504, such as a random access memory ("RAM") or other dynamic storage device coupled to the bus 500 for storing computer-readable instructions to be executed by the CPU 502. The main memory 504 may also be used for storing temporary variables or other intermediate information during execution of the instructions to be executed by the CPU 502. The server 408 may further include a read only memory ("ROM") 506 or other static storage device coupled to the bus 500 for storing static information and instructions for the CPU 502. A computer-readable storage device 508, such as a magnetic disk, optical disk, or solid state memory device, may be coupled to the bus 500 for storing information and instructions for the CPU 502.

The term "computer-readable instructions" as used above refers to any instructions that may be performed by the CPU 502 and/or other components. Similarly, the term "computer-readable medium" refers to any storage medium that may be used to store the computer-readable instructions. Such a medium may take many forms, including, but not limited to, non-volatile media, volatile media, and transmission media. Non-volatile media may include, for example, optical or magnetic disks, such as the storage device 508. Volatile media may include dynamic memory, such as main memory 504. Transmission media may include coaxial cables, copper wire and fiber optics, including wires of the bus 500. Transmission itself may take the form of acoustic or light waves, such as those generated during radio frequency ("RF") and infrared ("IR") data communications. Common forms of computer-readable media may include, for example, a floppy disk, a flexible disk, hard disk, magnetic tape, other magnetic medium, a CD ROM, DVD, other optical medium, a RAM, a PROM, an EPROM, a FLASH EPROM, other memory chip or cartridge, or any other medium from which a computer can read.

The CPU 502 may also be coupled via the bus 500 to a display 510 for displaying information to a user. One or more input devices 512, including alphanumeric and other keyboards, mouse, trackball, cursor direction keys, and so forth, may be coupled to the bus 500 for communicating information and command selections to the CPU 502. A network interface 514 provides two-way data communication between the server 408 and other computers over the network 406. In one example, the network interface 514 may be an integrated services digital network ("ISDN") card or a modem used to provide a data communication connection to a corresponding type of telephone line. As another example, the network interface 514 may be a local area network ("LAN") card used to provide a data communication connection to a compatible LAN. Wireless links may also be implemented via the network interface 514. In summary, the main function of the network interface 514 is to send and receive electrical, electromagnetic, optical, or other signals that carry digital data streams representing various types of information.

In accordance with the disclosed embodiments, an application 516 for determining an anatomical interval such as a BDI, or rather the computer-readable instructions therefor, may also reside on the storage device 508. The computer-readable instructions for the application 516 may then be executed by the CPU 502 and/or other components of the server 408 to determine a BDI or other anatomical intervals in the manner discussed above with respect to FIGS. 6-18. Such an application 516 may be implemented using any suitable application development environment and programming language known to those having ordinary skill in the art to carry out the steps of the algorithms disclosed and described in FIGS. 6-18. As noted above, in various embodiments, the application 516 may be a stand-alone application that may be executed independent of other applications, or it may be in the form of a plugin module to an existing software package, such as the open-source Osirix™ software package, and the like.

Other and further embodiments utilizing one or more aspects of the inventions described above can be devised without departing from the spirit of Applicant's invention. For example, the concepts can be applied to locating more than two anatomical features and can be applied to a variety of calculations than merely distance between two anatomical features, including without limitation alignment, planar orientation individually or collectively, absolute or relative anatomical angles; projection alignments of anatomical features, volume, and other results available from the digital images. The embodiments of the system and method for processing an image, compiling the images, and/or calculating and reporting the results, can be varied. The embodiments of the system and method can be included in combination with each other to produce variations of the disclosed methods and embodiments. The above described examples are nonlimiting and the anatomical features can vary with other embodiments not specifically noted. Further, the concepts of the searching for the anatomical features have been explained here within the exemplary context of the basion and dens and can be used with other anatomical features. Other variations are possible. The disclosed and undisclosed embodiments are not intended to limit or restrict the scope or applicability of the invention conceived of by the Applicant, but rather, in conformity with the patent laws, Applicant intends to fully protect all such modifications and improvements that come within the scope or range of equivalent of the following claims.

Discussion of singular elements can include plural elements and vice-versa. References to at least one item followed by a reference to the item may include one or more items. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The term "coupled," "coupling," "coupler," and like terms are used broadly herein and may include any method or device for securing, binding, bonding, fastening, attaching, joining, inserting therein, forming thereon or therein, communicating, or otherwise associating, for example, mechanically, magnetically, electrically, chemically, fluidicly, directly or indirectly with interim elements, one or more pieces of members together and may further include without limitation integrally forming one functional member with another in a unity fashion. The coupling may occur in any direction, including rotationally.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

What is claimed:

1. A method of determining a basion-dens interval from a set of digital images of an occipital-cervical area, comprising:
   identifying a first anatomical region in proximity to a basion;
   identifying a first bone of the first anatomical region coupled to the basion;
   processing a first image of the set of digital images, comprising:
      electronically searching along the first bone by progressively searching for bone pixels to determine a first image position of a preselected portion of the basion;
   identifying a second anatomical region in proximity to a dens;
   identifying a second bone of the second anatomical region coupled to the dens;
   processing the first image of the set of digital images, comprising:
      electronically searching along the second bone by progressively searching for bone pixels to determine a first image position of a preselected portion of the dens;
   repeating the processing of the first image on a second image of the set of digital images to find a second image position of the preselected portion of the basion and a second image position of the preselected portion of the dens, the first and second images defining a processed first subset of images;
   compiling the first and second image positions of the preselected portion of the basion and the first and second image positions of the preselected portion of the dens to produce a compiled position of the preselected portion of the basion and a compiled position of the preselected portion of the dens from the subset of images, wherein the compiling comprises comparing the first and second image positions of the preselected portion of the basion and first and second image positions of the preselected portion of the dens in the subset of images; and
   computing a distance between the preselected portion of the basion and the preselected portion of the dens from the compiled position of the preselected portion of the basion and the compiled position of the preselected portion of the dens to establish a computed basion-dens interval ("BDI").

2. The method of claim 1, wherein identifying the first anatomical region in proximity to the basion comprises:
   processing the first image of the set of digital images; and
   electronically identifying the first anatomical region.

3. The method of claim 1, wherein identifying the second anatomical region in proximity to the dens comprises:
   processing the first image of the set of digital images; and
   electronically identifying the second anatomical region.

4. The method of claim 1, wherein identifying the first bone in the first anatomical region coupled to the basion comprises:
   processing the first image of the set of digital images; and
   electronically searching in a first direction in the first anatomical region to find a bone pixel representing the first bone, the first bone including the basion.

5. The method of claim 4, wherein identifying the second bone in the second anatomical region coupled to the dens comprises:
   processing the first image of the set of digital images; and
   electronically searching in a second direction to find a bone pixel representing a second bone in the second anatomical region, the second bone including the dens.

6. The method of claim 1, wherein identifying the second bone in the second anatomical region coupled to the dens comprises:
   processing the first image of the set of digital images; and
   electronically searching in the second anatomical region to find a bone pixel representing the second bone, the second bone including the dens.

7. The method of claim 1, wherein electronically searching comprises processing in a direction from a first pixel to a second pixel to find a bone pixel and incrementally moving to the second pixel if the pixel is a bone pixel or processing in a different direction to a third pixel if the second pixel is not a bone pixel.

8. The method of claim 1, further comprising establishing a pixel intensity threshold for at least one of the images to establish a pixel intensity representing a bone pixel.

9. The method of claim 8, wherein establishing the pixel intensity comprises:
   scanning a plurality of pixels of at least one of the anatomical regions of the at least one of the images;
   mathematically assigning a comparative value of pixel intensity to the pixels;
   counting the number of pixels at a given pixel intensity;
   creating a histogram of pixel intensities with pixel intensities separated into ranges of pixel intensities;
   identifying a majority range of pixel intensities having at least a majority of the pixels that are not blank pixels;
   selecting a pixel intensity that is more than the majority range as the pixel intensity for a bone pixel.

10. The method of claim 8, wherein establishing the pixel intensity comprises:
    scanning a plurality of pixels within at least one of the anatomical regions of the at least one of the images;
    mathematically assigning a comparative value of pixel intensity to the pixels;
    counting the number of pixels at a given pixel intensity;
    identifying the lowest pixel intensity of the largest number of pixels that are not blank pixels;
    selecting a pixel intensity that is more than the lowest pixel intensity of the largest number of pixels to represent a pixel intensity of a bone.

11. The method of claim 1, comprising establishing a pixel intensity threshold for at least one of the images to establish a pixel intensity representing a non-bone pixel.

12. The method of claim 1, wherein the digital images comprise pixels and further comprising:
    scanning a plurality of pixels of at least one of the anatomical regions of the at least one of the images;
    mathematically assigning a comparative value of pixel intensity to the pixels;
    establishing a pixel gradient for at least some of the pixels; and
    wherein electronically searching comprises searching in a direction of a maximum change in pixel gradient from pixel to pixel.

13. The method of claim 12, wherein establishing the pixel gradient comprises:
   determining a pixel intensity of a first pixel;
   determining a pixel intensity of pixels around the first pixel; and
   determining a gradient of change of pixel intensity from the first pixel to the pixels around the first pixel.

14. The method of claim 12, wherein establishing the pixel gradient comprises:
   determining a pixel intensity of a first pixel at a first position;
   determining a pixel intensity of pixels around the first pixel; and
   calculating a position of an intensity centroid according to the formula:

Centroid coordinate = sum of [(pixel coordinate) * (pixel intensity)]/ sum of pixel intensities.

15. The method of claim 14, wherein the intensity centroid position is defined in an orthogonal coordinate system.

16. The method of claim 1, selecting a second subset of images of the set of digital images having at least one image different than the first subset of images to determine the BDI.

17. The method of claim 1, comprising comparing the computed BDI with normative BDI data; and
   reporting results of the computed BDI that is compared with normative BDI data.

18. The method of claim 1, further comprising searching for basion first and then the dens.

19. The method of claim 1, further comprising searching for the dens first and then the basion.

20. The method of claim 1, wherein compiling results from the processed first subset of images further comprises preselecting images to compile by:
   fitting a mathematical function to values of coordinates of an anatomical region in a plurality of the processed images;
   computing a peak of the mathematical function; and
   selecting a processed image having the value of the coordinate of the anatomical region in proximity to the peak.

21. The method of claim 20, further comprising analyzing a different subset of digital images if the images do not contain a value of a coordinate corresponding to the peak.

22. The method of claim 20, further comprising comparing images on either side of the processed image that is selected to determine the compiled position for the preselected portion of the basion, preselected portion of the dens, or a combination thereof for the BDI.

23. A system for determining a basion-dens interval from a set of digital images of an occipital-cervical area, comprising:
   an electronic processor;
   a storage device in communication with the processor, the storage device having computer-readable instructions stored thereon, the computer-readable instructions comprising instructions for causing the processor to carry out the method according to claim 1.

24. A computer readable non-volatile media for determining a basion-dens interval from a set of digital images of an occipital-cervical area, comprising computer readable instructions for causing a computer to perform the steps of claim 1.

25. A method of determining a basion-dens interval from a set of digital images of an occipital-cervical area, comprising:
   processing a first image of the set of images, comprising:
      identifying a first anatomical region in proximity to a basion;
      electronically searching in a first direction to find a bone pixel that defines a first bone;
      electronically searching along the first bone in a second direction by progressively searching for bone pixels to determine a first image position of a preselected portion being an inferior portion of the basion;
      identifying a second anatomical region in proximity to a dens;
      electronically searching in a third direction to find a bone pixel that defines a second bone in the second anatomical region; and
      electronically searching along the second bone in a fourth direction by progressively searching for bone pixels to determine a first image position of a preselected portion being a superior portion of the dens;
   changing to at least a second image of the set of images and repeating the processing steps for the second image to find a second image position of the preselected portion of the basion and a second image position of the preselected portion of dens so that with at least the first image, the processing forms a processed first subset of images;
   compiling results from the subset of images to find a compiled position of the preselected portion of the basion and a compiled position of the preselected portion of the dens from the subset of images, comprising:
      comparing image positions of at least two of the images in the subset of images; and
      selecting the position of the preselected portion of the basion and the position of the preselected portion of the dens from the image positions that maximize a distance between the basion and the dens;
   computing a distance between the preselected portion of the basion and the preselected portion of the dens to establish a computed basion-dens interval ("BDI").

* * * * *